(12) United States Patent
Huvelle et al.

(10) Patent No.: US 7,062,326 B2
(45) Date of Patent: *Jun. 13, 2006

(54) METHOD AND APPARATUSES FOR MONITORING HEMODYNAMIC ACTIVITIES USING AN INTRACARDIAC IMPEDANCE-DERIVED PARAMETER

(75) Inventors: Etienne Huvelle, Frasnes-lez-Gosselies (BE); Francisca Cuesta Sanchez, Machelen (BE)

(73) Assignee: Cardiac Pacemakers, Inc., Saint Paul, MN (US)

( * ) Notice: Subject to any disclaimer, the term of this patent is extended or adjusted under 35 U.S.C. 154(b) by 102 days.

This patent is subject to a terminal disclaimer.

(21) Appl. No.: 10/359,820

(22) Filed: Feb. 6, 2003

(65) Prior Publication Data

US 2003/0114889 A1 Jun. 19, 2003

Related U.S. Application Data

(63) Continuation of application No. 09/616,858, filed on Jul. 14, 2000, now Pat. No. 6,522,914.

(51) Int. Cl.
*A61N 1/365* (2006.01)

(52) U.S. Cl. .............................. 607/18; 607/17; 607/9; 607/28

(58) Field of Classification Search .................. 607/9, 607/11, 17–19, 28; 600/509, 536
See application file for complete search history.

(56) References Cited

U.S. PATENT DOCUMENTS

| | | | |
|---|---|---|---|
| 3,593,718 A | 7/1971 | Krasner | 607/20 |
| 4,009,721 A | 3/1977 | Alcidi | 607/22 |

(Continued)

FOREIGN PATENT DOCUMENTS

DE 2805482 A1 3/1987

(Continued)

OTHER PUBLICATIONS

Alt, Eckhard., "What is the Ideal Rate–Adaptive Sensor for Patients with Implantable Cardioverter Defibrillators: Lessons from Cardiac Pacing", *Am. J. Cardiol.*, 83, (1999), 17D–23D.

(Continued)

*Primary Examiner*—Carl Layno
(74) *Attorney, Agent, or Firm*—Schwegman, Lundberg, Woessner & Kluth, P.A.

(57) ABSTRACT

An intracardiac impedance-derived parameter, Half Cycle Activity (HCA) is used in sensing and controlling cardiac activities in implantable cardiac devices such as bradycardia pacemakers and cardioverter defibrillators. This impedance-derived parameter correlates closely with physical workload and at the same time provides hemodynamic feedback information. Thus, it allows a pacemaker system to implement accurately an increase in hemodynamically driven pacing rate, as well as to limit an inappropriate decrease of driven pacing rate advised by another sensor such as an accelerometer. In addition, it determines the maximum pacing rate for the pacemaker so as to prevent hemodynamic compromise. Therefore, the HCA parameter may be used to determine a Hemodynamic Upper Rate Limit and a Hemodynamic Lower Rate Limit, and thus define a Hemodynamic Pacing Range that is compatible with the range of physiological rate. This allows a closed-loop control of the pacing rate. In an implantable cardioverter defibrillator system, the hemodynamic tolerance of arrhythmias can also be assessed by using the HCA parameter to adjust therapy provided to a heart, such as antitachycardia pacing and/or cardioverting shocks.

20 Claims, 22 Drawing Sheets

U.S. PATENT DOCUMENTS

| | | | |
|---|---|---|---|
| 4,140,132 A | 2/1979 | Dahl | 607/19 |
| 4,228,803 A | 10/1980 | Rickards | 607/25 |
| 4,291,699 A | 9/1981 | Geddes et al. | 178/419 D |
| 4,399,820 A | 8/1983 | Wirtzfeld et al. | 607/21 |
| 4,428,378 A | 1/1984 | Anderson et al. | 607/19 |
| 4,510,944 A | 4/1985 | Porges | 600/500 |
| 4,543,954 A | 10/1985 | Cook et al. | 607/21 |
| 4,562,843 A | 1/1986 | Djordjevich et al. | 600/485 |
| 4,596,251 A | 6/1986 | Plicchi et al. | 607/20 |
| 4,686,987 A | 8/1987 | Salo et al. | 607/24 |
| 4,702,253 A | 10/1987 | Nappholz et al. | 607/20 |
| 4,722,351 A | 2/1988 | Phillipps et al. | 600/509 |
| 4,773,401 A | 9/1988 | Citak et al. | 128/419 PG |
| 4,781,201 A | 11/1988 | Wright et al. | 600/484 |
| 4,858,611 A | 8/1989 | Elliott | 607/20 |
| 4,899,752 A | 2/1990 | Cohen | 607/23 |
| 4,901,725 A | 2/1990 | Nappholz et al. | 607/17 |
| 4,966,146 A | 10/1990 | Webb et al. | 607/19 |
| 5,027,813 A | 7/1991 | Pederson et al. | 607/19 |
| 5,063,927 A | 11/1991 | Webb et al. | 607/18 |
| 5,074,303 A | 12/1991 | Hawk et al. | 607/17 |
| 5,085,215 A | 2/1992 | Nappholz et al. | 607/17 |
| 5,085,583 A | 2/1992 | Amos et al. | 439/479 |
| 5,137,019 A | 8/1992 | Pederson et al. | 607/20 |
| 5,156,147 A | 10/1992 | Warren et al. | 607/24 |
| 5,174,286 A | 12/1992 | Chirife | 607/11 |
| 5,179,946 A | 1/1993 | Weiss | 607/4 |
| 5,190,035 A | 3/1993 | Salo et al. | 607/24 |
| 5,197,467 A | 3/1993 | Steinhaus et al. | 607/20 |
| 5,201,808 A | 4/1993 | Steinhaus et al. | 607/20 |
| 5,235,237 A | 8/1993 | Leonhardt | 310/329 |
| 5,235,976 A | 8/1993 | Spinelli | 607/32 |
| 5,249,572 A | 10/1993 | Bonnet | 607/20 |
| 5,271,395 A | 12/1993 | Wahlstrand et al. | 607/9 |
| 5,273,034 A | 12/1993 | Nilsson | 607/18 |
| 5,284,136 A | 2/1994 | Hauck et al. | 607/24 |
| 5,300,093 A | 4/1994 | Koestner et al. | 607/127 |
| 5,303,702 A | 4/1994 | Bonnet et al. | 607/20 |
| 5,314,449 A | 5/1994 | Lindgren | 607/24 |
| 5,318,597 A | 6/1994 | Hauck et al. | 607/20 |
| 5,383,473 A | 1/1995 | Moberg | 128/782 |
| 5,391,190 A | 2/1995 | Pederson et al. | 607/23 |
| 5,423,870 A | 6/1995 | Olive et al. | 607/18 |
| 5,423,883 A | 6/1995 | Helland | 607/127 |
| 5,431,687 A | 7/1995 | Kroll | 607/8 |
| 5,431,693 A | 7/1995 | Schroeppel | |
| 5,441,524 A | 8/1995 | Rueter et al. | 607/18 |
| 5,469,859 A * | 11/1995 | Tsoglin et al. | 600/536 |
| 5,480,412 A | 1/1996 | Mouchawar et al. | 607/17 |
| 5,490,323 A | 2/1996 | Thacker et al. | 29/825 |
| 5,501,702 A | 3/1996 | Plicchi et al. | 607/20 |
| 5,507,785 A | 4/1996 | Deno | 607/24 |
| 5,511,554 A | 4/1996 | Helfenbein et al. | |
| 5,522,860 A | 6/1996 | Molin et al. | 607/20 |
| 5,524,632 A | 6/1996 | Stein et al. | 600/546 |
| 5,531,772 A | 7/1996 | Prutchi | 607/17 |
| 5,560,370 A | 10/1996 | Verrier et al. | |
| 5,562,711 A | 10/1996 | Yerich et al. | 607/17 |
| 5,562,712 A | 10/1996 | Steinhaus et al. | 607/20 |
| 5,626,622 A | 5/1997 | Cooper | 607/18 |
| 5,626,624 A | 5/1997 | Schaldach et al. | 607/24 |
| 5,685,316 A | 11/1997 | Schookin et al. | 128/734 |
| 5,713,933 A | 2/1998 | Condie et al. | 607/28 |
| 5,722,997 A | 3/1998 | Nedungadi et al. | 607/28 |
| 5,766,225 A | 6/1998 | Kramm | |
| 5,782,884 A | 7/1998 | Stotts et al. | 607/17 |
| 5,792,194 A | 8/1998 | Morra | 607/17 |
| 5,800,470 A | 9/1998 | Stein et al. | 607/20 |
| 5,817,135 A | 10/1998 | Cooper et al. | 607/17 |
| 5,817,136 A | 10/1998 | Nappholz et al. | 607/17 |
| 5,824,020 A | 10/1998 | Cooper | 607/17 |
| 5,824,029 A | 10/1998 | Weijand et al. | 607/122 |
| 5,836,975 A | 11/1998 | DeGroot | 607/5 |
| 5,836,976 A | 11/1998 | Min et al. | 607/6 |
| 5,978,707 A | 11/1999 | Krig et al. | |
| 6,006,134 A | 12/1999 | Hill et al. | |
| 6,015,388 A | 1/2000 | Sackner et al. | |
| 6,022,322 A | 2/2000 | Prutchi | 600/506 |
| 6,044,294 A | 3/2000 | Mortazavi et al. | 600/547 |
| 6,049,735 A | 4/2000 | Hartley et al. | 607/9 |
| 6,076,015 A | 6/2000 | Hartley et al. | 607/20 |
| 6,151,524 A | 11/2000 | Krig et al. | |
| 6,161,042 A | 12/2000 | Hartley et al. | 607/20 |
| 6,179,865 B1 | 1/2001 | Hsu et al. | 600/518 |
| 6,317,632 B1 | 11/2001 | Krig et al. | |
| 6,370,424 B1 | 4/2002 | Prutchi | 600/547 |
| 6,415,183 B1 | 7/2002 | Scheiner et al. | |
| 6,459,929 B1 * | 10/2002 | Hopper et al. | 600/513 |
| 6,463,326 B1 | 10/2002 | Hartley et al. | 607/20 |
| 6,522,917 B1 | 2/2003 | Hsu et al. | 600/518 |
| 6,647,289 B1 | 11/2003 | Prutchi | 600/547 |
| 2002/0107552 A1 | 8/2002 | Krig et al. | |
| 2002/0123768 A1 | 9/2002 | Gilkerson | |
| 2002/0123769 A1 | 9/2002 | Panken et al. | 607/9 |
| 2003/0069609 A1 | 4/2003 | Thompson | 607/14 |
| 2003/0105499 A1 | 6/2003 | Hartley et al. | 607/17 |
| 2003/0109792 A1 | 6/2003 | Hsu et al. | 600/518 |
| 2004/0049237 A1 | 3/2004 | Larson et al. | 607/17 |
| 2004/0102908 A1 | 5/2004 | Larson et al. | 202/45 |
| 2004/0116820 A1 | 6/2004 | Daum et al. | 600/547 |
| 2005/0004610 A1 | 1/2005 | Kim et al. | |

FOREIGN PATENT DOCUMENTS

| | | |
|---|---|---|
| EP | 0003567 | 8/1979 |
| EP | 447024 A2 | 9/1991 |
| EP | 0555988 | 8/1993 |
| EP | 702977 A2 | 3/1996 |
| EP | 744190 A2 | 11/1996 |
| EP | 765632 A2 | 4/1997 |
| FR | 2305168 | 10/1976 |
| WO | WO-9406512 A1 | 3/1994 |
| WO | WO-98/14240 | 4/1998 |
| WO | WO-9943385 | 9/1999 |

OTHER PUBLICATIONS

Barold, S..,et al. ,"Contemporary Issues in Rate–Adaptive Pacing", *Clin. Cardiol., 20*, (1997), 726–729.

Johnston, P..W. ,et al. ,"The Transthoracic Impedance Cardiogram is a Potential Haemodynamic Sensor for an Automated External Defibrillator", *European Heart Journal, 19*, (1998), 1879–1888.

Rickards, Anthony.,et al. ,"An Implantable Intracardiac Accelerometer for Monitoring Myocardial Contractility", *PACE*, vol. 19, Part 1, (Dec. 1996),2066–2071.

Salo, Rodney,W.,"Measurement of Ventricular Volume by Intracardiac Impedance: Theoretical and Empirical Approaches", *IEEE Transactions on Biomedical Engineering*, vol. BM#–33, #2,(Feb. 1986), 189–195.

Schaldach, M..,"Automatic Adjustment of Pacing Parameters Based on Intracardiac Impedance Measurements", *PACE*, vol. 13, Part II,(Dec. 1990), 1702–1710.

Krig, David B., "Apparatus and Method For Treating Ventricular Tachyarrhythmias", Application Ser. No. 11/073,818, Filed Mar. 7, 2005, 61 pp.

Eular, D. E., et al., "Inspiration Induced by Phrenic Nerve Stimulation Increases Defibrillation Energy Requirements", *PACE(22), Part II, Abstract No. 307,* (1999), 777.

Freeberg, S., "Cross–Checking of Transthoracic Impedance and Acceleration Signals", US Appl. Ser. 10/696,729, filed Oct. 29, 2003.

Hauck, J. A., "A Minute Ventilation Sensor Derived from Intra–thoracic Electric Impedance as a Cardiac Pacemaker Rate Modulator", *University of Minnesota Master Thesis*, (Jun. 1993), pp. 80–86 & 97.

Hayano, J. et al., "Respiratory Sinus Arrhythmia: A Phenomenon Improving Pulmonary Gas Exchange and Circulatory Efficiency", *Circulation*, 94(4), (1996), 842–847.

Hsu, W., "System and Method for Classifying Tachycardia Arrhythmias Having 1:1 Atrial to Ventricular Rhythms", US Appl. Ser. No. 09/417,588, Filed on Oct. 13, 1999 39 pgs.

Jackson, Leland B., "Chapter 11 / Quantization Effects", In: *Digital Filters and Signal Processing*, 2d Edition, Kluwer Academic Publishers,(1989), 297–340.

Kim, J. et al., "Cardiac Cycle Synchronized Sampling of Impendance Signal", US Appl. No. 10/612,381, Filed Jul. 2, 2003, 26 pp.

Lincoln, William C., "Classifying Tachyarrhythmia Using Time Interval Between Ventricular Depolarization and Mitral Valve Closure", *Application Ser. No. 10/618,261*, filed Jul. 11, 2003.

Ruiter, J H., et al., "Adaptive rate pacing controlled by the right ventricular preejection interval: Clinical experience with a physiological pacing system", *PACE*, 15(6), (Jun. 1992),886–894.

Salo, R W., "The theoretical basis of a computational model for the determination of volume by impedance", *Automedica, 11*, (1989),299–310.

Schaldach, M, et al., "Intracardiac impedance to determine sympathetic activity in rate responsive pacing", *PACE*, 15(11 Pt 2), (Nov. 1992), 1778–1786.

Stahmann, J. E., et al., "Implantable Devices and Methods Using Frequency–Domain Analysis of Thoracic Signal", U.S. Appl. No. 10/612,387, filed Jul. 2, 2003, 39 pages.

Sweeney, R. J., et al., "Device for Monitoring Fluid Status", U.S. Appl. No. 10/909,926, filed Aug. 2, 2004, 17 pages.

Zhang, Y., et al., "Methods and Apparatuses for Arrhythmia Detection and Classification Using Wireless ECG", U.S. Appl. No. 10/975,166, filed Oct. 28, 2004, 69 pages.

* cited by examiner

WHEN $N_i$ IS EVEN

WHEN $N_i$ IS ODD

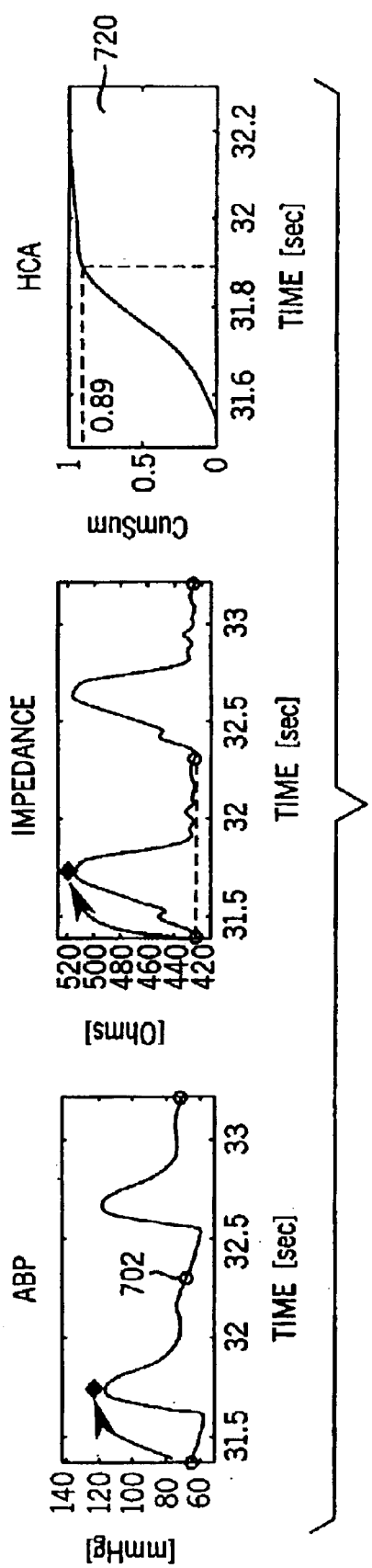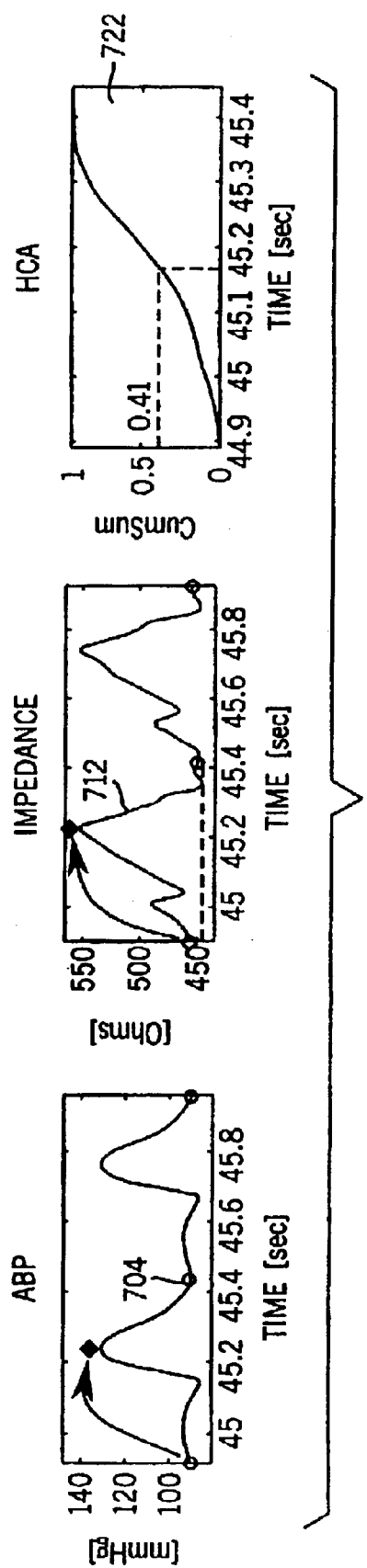
FIG. 7a
FIG. 7b

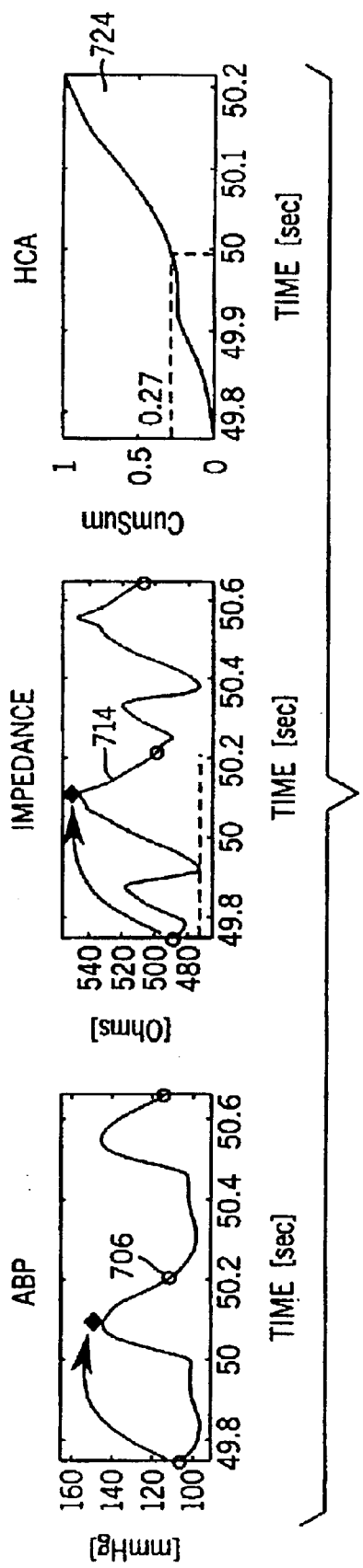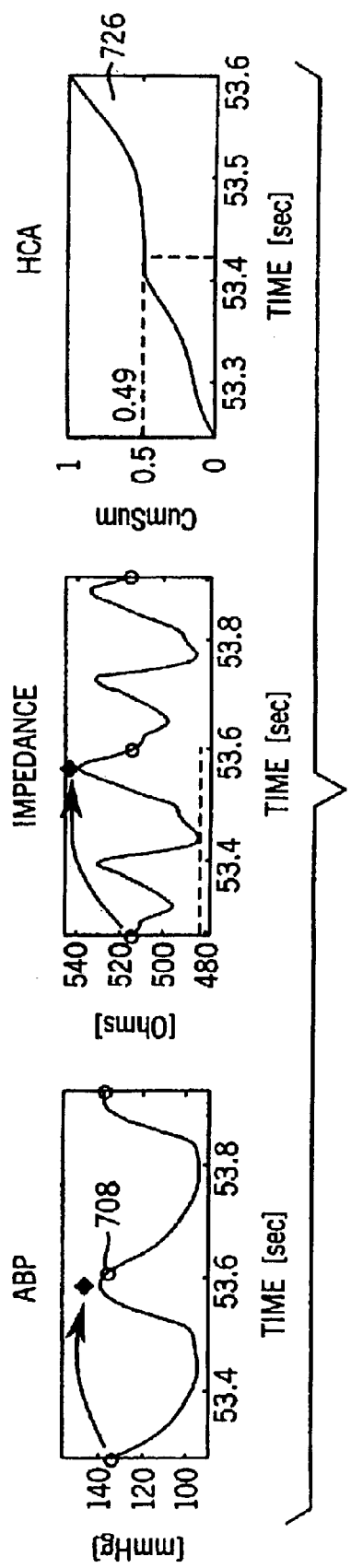
FIG. 7c
FIG. 7d

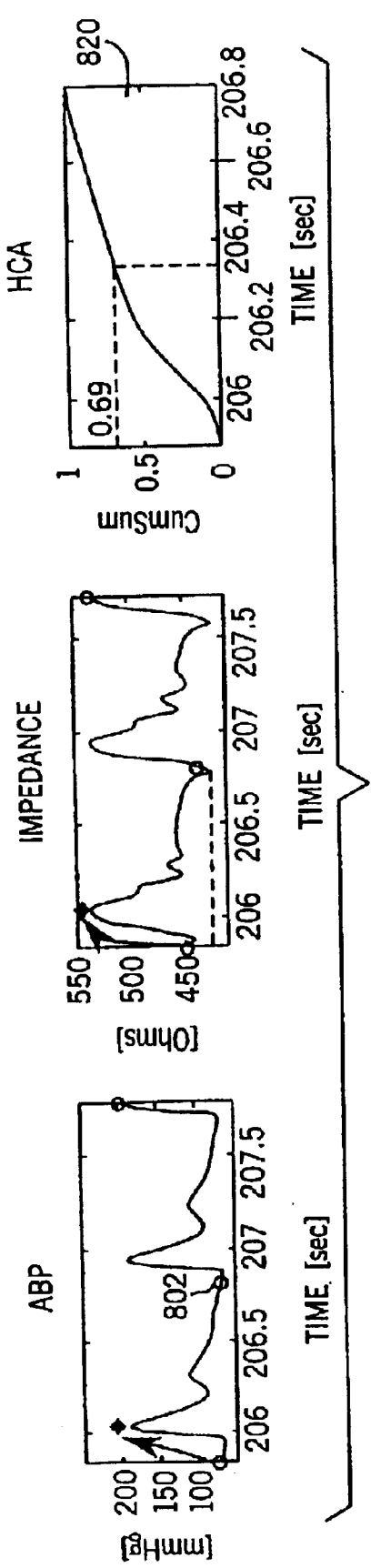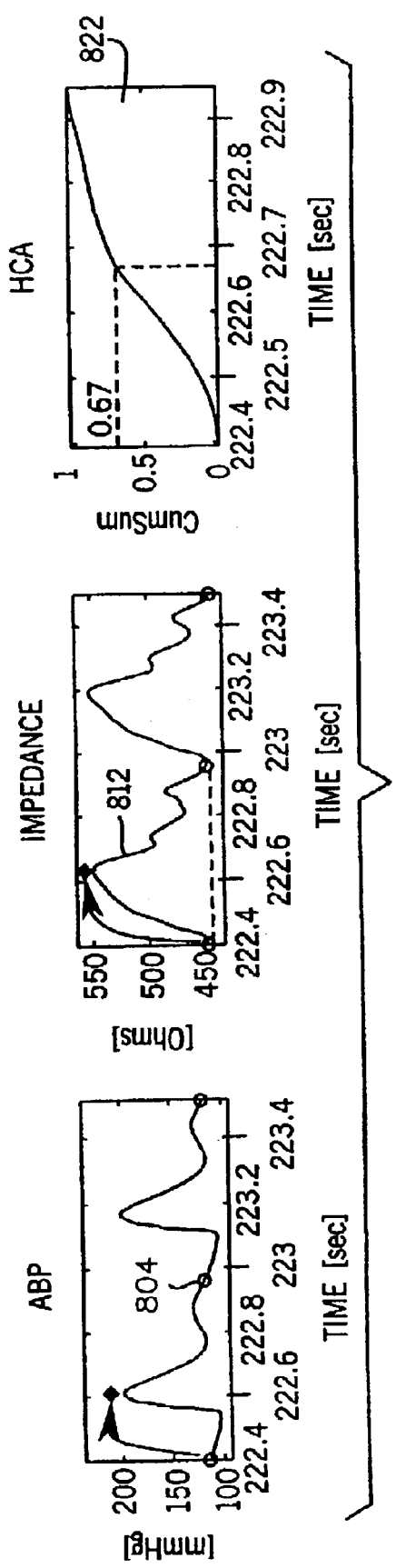
FIG. 8a
FIG. 8b

METHOD AND APPARATUSES FOR MONITORING HEMODYNAMIC ACTIVITIES USING AN INTRACARDIAC IMPEDANCE-DERIVED PARAMETER

CROSS-REFERENCE TO RELATED APPLICATION(S)

This application is a continuation of U.S. application Ser. No. 09/616,858, filed on Jul. 14, 2000, now issued as U.S. Pat. No. 6,522,914, the specification of which is incorporated herein by reference.

FIELD OF THE INVENTION

This invention relates in general to sensing and controlling cardiac activities in implantable devices including, but not limited to, bradycardia pacemakers and cardioverter defibrillators. More particularly, the invention concerns such a device in which an intracardiac impedance-derived parameter, Half Cycle Activity (HCA) is used as a key variable.

BACKGROUND OF THE INVENTION

It is a well-recognized challenge to monitor accurately physical demands on cardiac support imposed by different levels of work or exercise a patient engages in (Barold et al., Clin Cardiol (1997), Vol 20 (8): 726–9; Alt, Am J Cardiol (1999), Vol 83(5B): 17D–23D). And yet, it is essential for a cardiac pacemaker to operate at a pacing rate that correlates with the workload presented. It is equally essential for a cardioverter defibrillator to determine hemodynamic status of a patient before diagnosing a life-threatening arrhythmia and exerting ventricular anti-tachy therapy (Johnston et al., Eur Heart J (1998), Vol. 19 (12):1879–88). A variety of physiologic or non-physiologic sensors have been designed during the last two decades to produce a signal directly related to the metabolic demand, including blood pH (U.S. Pat. No. 4,009,721), QT interval (U.S. Pat. No. 4,228,803), blood $O_2$ saturation (U.S. Pat. No. 4,399,820), blood temperature (U.S. Pat. No. 4,543,954), pressure sensor (U.S. Pat. Nos. 4,899,752 and 5,105,819), piezoelectric crystal (U.S. Pat. Nos. 4,140,132 and 4,428,378), accelerometer (U.S. Pat. Nos. 5,235,237 and 5,383,473), micro-accelerometer (U.S. Pat. Nos. 5,423,883, 5,480,412, Rickards et al., The Multicenter PEA Study Group—PACE (1996) 19:12 Pt1, 2066–2071), thoracic and intracardiac impedance (U.S. Pat. Nos. 3,593,718, 4,291,699, 4,773,401, 5,085,583, 5,235,976, 5,562,711 and 5,782,884) etc. These sensors are less than optimal and have led to little commercial success for various reasons, including difficulty to implement due to the need for specific hardware, lack of correlation between the signal and actual workload, lack of hemodynamic feedback information, slow response, and lack of robustness, i.e., high sensitivity to noise or artifacts inherent to the signal.

SUMMARY OF THE INVENTION

To resolve the above problems, the present invention is directed to an improved method and apparatus for monitoring hemodynamic activities in implantable cardiac devices. In particular, the present invention relates to cardiac pacemakers, cardioverter defibrillators and like devices that use a physiologic sensing parameter, Half Cycle Activity (HCA) to monitor and adjust cardiac activities.

In accordance with one aspect of the invention, the impedance-derived parameter HCA correlates closely with the workload and at the same time provides hemodynamic feedback information. Thus, it allows a pacemaker system to implement accurately an increase in hemodynamically driven pacing rate, as well as to limit an inappropriate decrease of driven pacing rate advised by another sensor such as an accelerometer. On the other hand, it determines the maximum pacing rate for the pacemaker, thus preventing hemodynamic compromise from occurring.

In accordance with another aspect of the invention, this intracardiac impedance-derived parameter HCA is resistant to noise or artifacts. Unlike other sensing parameters, HCA measurement is based on the whole impedance waveform; therefore, it is robust to local artifacts. Additionally, HCA is based on a baseline-corrected impedance signal; thus, it is much more resistant to baseline shifts than other impedance-derived parameters.

In accordance with yet another aspect of the present invention, the implementation of such parameter, in particular HCA, uses a single bipolar ventricular pacing and sensing lead in a pacemaker or defibrillator. Such a ventricular lead is connected to a sensing module to gather sensed physiological events. Specifically, an impedance reading module connected to the ventricular lead reads impedance signals, which is directed to the HCA microprocessor, where HCA computation takes place in real time. The result of HCA values is then fed back into a pacing controller module, which through a pacing module completes the adjustment to the cardiac stimulating events such as the pacing rates.

The present invention with all aspects of an impedance-derived parameter such as HCA, therefore, brings significant improvements in cardiac activity management devices.

BRIEF DESCRIPTION OF THE DRAWINGS

The foregoing features and other aspects of the present invention will become better understood by reference to the accompanying drawings and following description, where:

FIGS. 7(a)–7(e) are illustrations of artery blood pressure (ABP) waveforms and intracardiac impedance waveforms for two cardiac cycles along with the plots for HCA computation for the first cardiac cycle recorded at different pacing rates;

FIGS. 8(a)–8(e) are illustrations of ABP waveforms and intracardiac impedance waveforms for two cardiac cycles after dobutamine injection along with the plots for HCA computation for the first cardiac cycle recorded at different pacing rates;

DETAILED DESCRIPTION OF THE DRAWINGS

Figure 1:
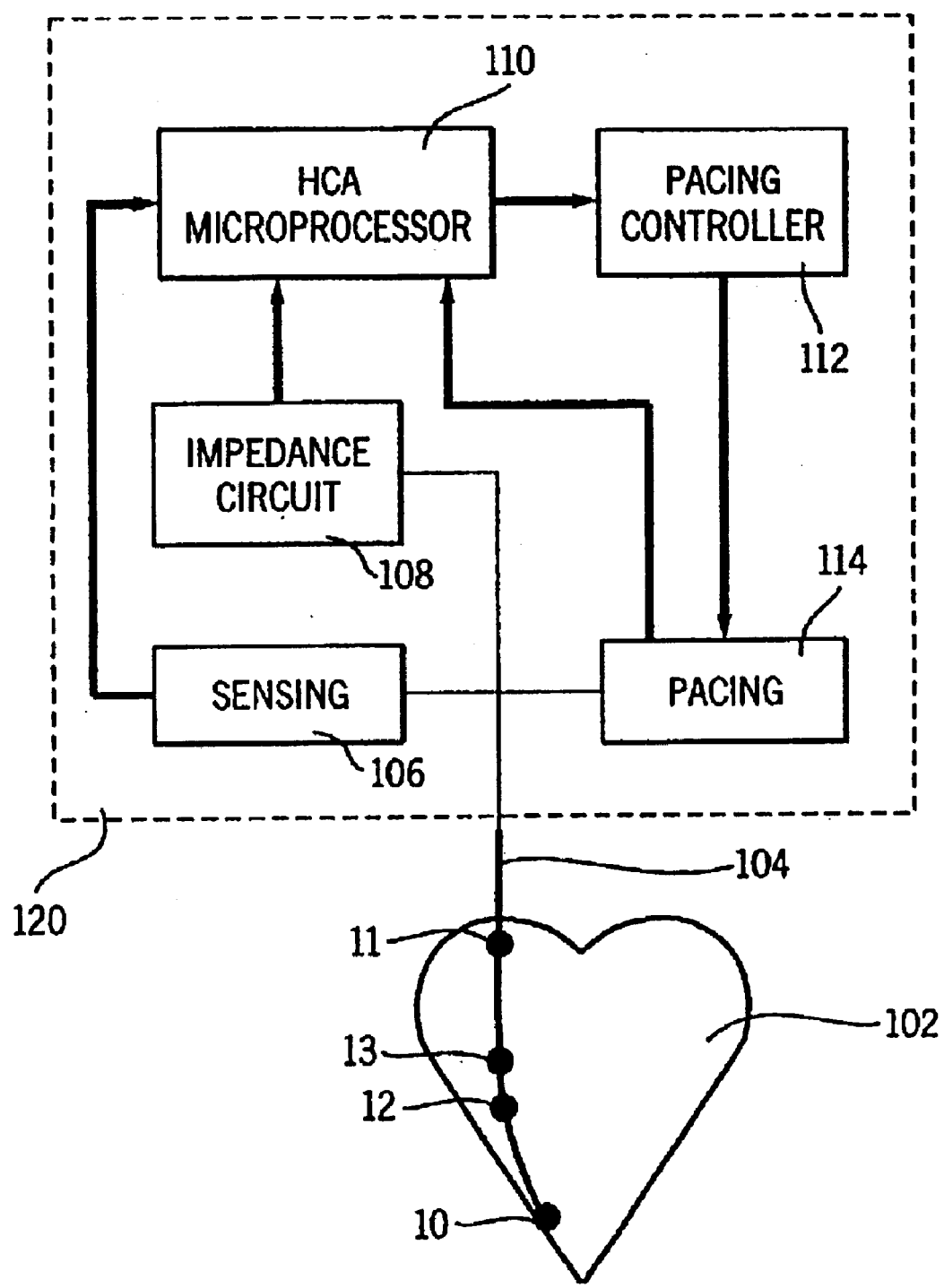
FIG. 1 is a block diagram showing a preferred embodiment of this invention.

Intracardiac impedance measurements are deemed to be a function of the volume of the heart; therefore, they reflect physiological demands on the heart. (Salo, Automedica, 1989, Vol. 11, 299–310; Ruiter et al., PACE, 1992, Vol. 15, 886–894; Schaldach et al., PACE, 1992, Part II, Vol. 15, 1778–1786.) Referring to FIG. 1, FIG. 1 is a representation of the heart 102 where an endocardial lead 104 has been implanted in the right ventricle. Lead 104 includes electrodes, including a tip electrode 10, generally disposed at the apex of the right ventricle, and other electrodes 11, 12, and 13, disposed proximally to the tip. In a general four terminal configuration, a signal is injected between electrodes 10 and 11, and a signal is recorded between electrodes 12 and 13. In another preferred embodiment, the injection and recording of the electrical signal can involve three or only two electrodes (respectively three and two terminal configurations). In the latter case, one single bipolar pacing and sensing ventricular lead is used. In general, an n terminal configuration can be constituted by n electrodes located in one or several leads and the pacemaker or cardioverter-defibrillator can. The apparatus described by Prutchi (U.S. Pat. No. 5,531,772) or Deno (U.S. Pat. No. 5,507,785) can be used but it should be understood that other apparatus and methods for detecting change in impedance could also be used. Various pacing modes where a ventricular lead is provided can be used, including VVI, VVIR, VDDR, and DDDR. These standard operating modes of a pacemaker are subscribed by North American Society of Pacing and Electrophysiology (NASPE) and British Pacing and Electrophysiology Group (BPEG). VVI stands for ventricular pacing, ventricular sensing, inhibited when sensing a ventricular event; VVIR stands for ventricular pacing, ventricular sensing, inhibited when sensing a ventricular event, rate responsive ventricular pacing; VDDR stands for ventricular pacing, atrial and ventricular (dual) sensing, atrioventricular (dual) synchronous pacing, rate responsive ventricular pacing; and DDDR stands for atrial and ventricular (dual) pacing, atrial and ventricular (dual) sensing, atrioventricular (dual) synchronous pacing, rate responsive pacing.

This embodiment of the invention involves continuous measurement of ventricular impedance signals. An intracardiac impedance derived parameter, Half Cycle Activity (HCA) is provided according to the invention. As shown in FIG. 1, a preferred embodiment of this invention includes the ventricular lead 104 in the heart 102, a Sensing module 106, a Pacing module 114, an Impedance Reading module 108, a Pacing Controller 112 and an HCA Microprocessor 110. Ventricular lead 104 directs the cardiac signals to the sensing module 106, as well as to module 108, where the impedance values are read. The recorded impedance signals are then channeled to HCA Microprocessor 110 for HCA computation in real time. The resulting HCA values for each cardiac cycle are used by the Pacing Controller 112 to adjust the pacing rate as needed. In a variant of this embodiment, this feedback mechanism allows another type of controller, such as a Defibrillating Controller in a cardiac defibrillator, in place of Pacing Controller 112, to adjust therapy, anti-tachycardia pacing and/or cardioverting-defibrillating shocks.

Figure 2:
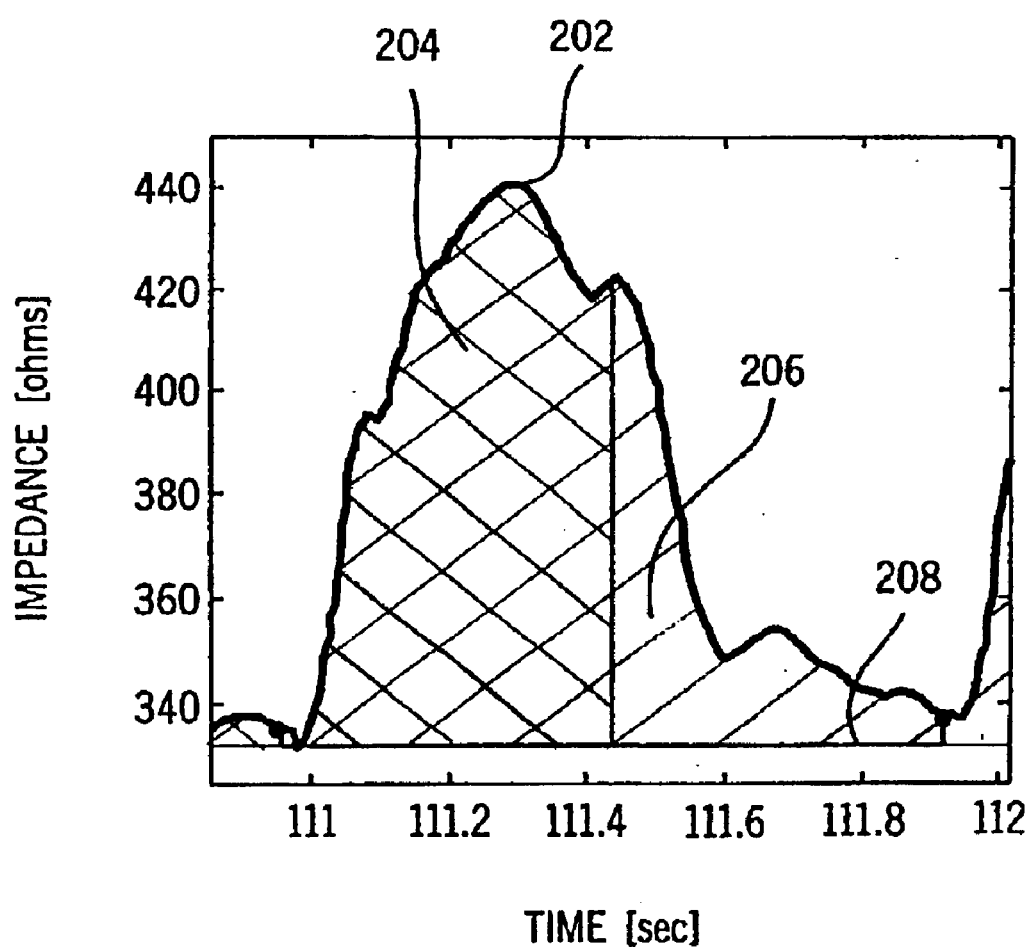
FIG. 2 illustrates an impedance waveform corresponding to a single cardiac cycle, with a ventricular rate (Vrate) of 60 ppm.

According to the present invention, HCA is defined as the ratio of the area encompassed by the first half of the impedance waveform and the area encompassed by the whole impedance waveform corresponding to a single cardiac cycle. Referring to FIG. 2, HCA corresponds to the dark-shaded area 204 divided by the sum of the dark-shaded area 204 and the light-shaded area 206 underneath the impedance wave form 202 of a single cardiac cycle. The area is measured with respect to a baseline level (208), which is the global minimum impedance in the cardiac cycle, to eliminate the differences between the cardiac cycles due to baseline shifts. More precisely, $z_{ij}$ stand for the j-th impedance signal sample in the i-th cardiac cycle of $N_i$ samples. The HCA parameter is defined as follows $$HCA_i = \frac{\sum_{j=1}^{N_i/2} \left[z_{ij} - \min_j(z_{ij})\right]}{\sum_{j=1}^{N_i} \left[z_{ij} - \min_j(z_{ij})\right]} \quad \text{for } i = 1, \ldots, m \quad [1]$$

where m is the number of cardiac cycles. A cardiac cycle is defined by two consecutive paced and/or sensed ventricular events.

As described above with respect to FIG. 1, the implementation of HCA measurement is carried out by the HCA Microprocessor 110. The specific steps in HCA Microprocessor 110 are as follows.

Figure 3A:
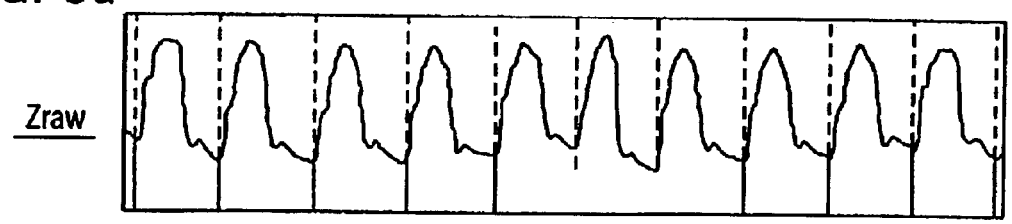
FIGS. 3(a), 3(b), and 3(c) are diagrams summarizing the signal processing steps for 1/HCA calculation, including the original ventricular impedance signal Zraw, refined signal Zproc, and 1/HCA values calculated from Zproc.
Figure 3B:

In a preferred embodiment of this invention, ventricular impedance sample signals are measured in real time as Zraw at a given sampling frequency, as shown in FIG. 3(a). This is done by Zraw Recorder 402 depicted in FIG. 4 and FIG. 5, which demonstrate two different implementations for HCA Microprocessor 110. To prevent pacing artifacts from distorting the impedance waveform, a procedure called blanking is adopted. It is carried out by a Blanking module 404 shown in FIG. 4 and FIG. 5. Blanking is a transient interruption of signal recording for a short period of time (e.g. 20–30 milliseconds). The interruption starts at the onset of a pacing spike. The duration of blanking must be long enough also to avoid discharging artifacts. Apace and Vpace markers are used in blanking atrial and ventricular pacing spikes. Blanking is then followed by padding, which replaces all non recorded samples during blanking with the last valid impedance signal. Padding occurs in a Padding module 406 also shown in FIGS. 4 and 5. After these refinement steps, the processed signals shown as Zproc in FIG. 3(b) are used to calculate HCA values for each cardiac cycle.

HCA can be computed according to equation [1], and the two variants of [1] listed as equations [2] and [3] for even or odd number of samples ($N_i$), respectively, in a series of cardiac cycles.

$$HCA_i = \frac{\sum_{j=1}^{N_i/2} z_{ij} - \frac{N_i}{2}\min_j(z_{ij})}{\sum_{j=1}^{N_i} z_{ij} - N_i \min_j(z_{ij})} \text{ for } i = 1, \ldots, m \text{ when } N_i \text{ is even} \quad [2]$$

$$HCA_i = \frac{\sum_{j=1}^{(N_i-1)/2} z_{ij} - \frac{N_i-1}{2}\min_j(z_{ij})}{\sum_{j=1}^{N_i} z_{ij} - N_i \min_j(z_{ij})} \text{ for } i = 1, \ldots, m \text{ when } N_i \text{ is odd} \quad [3]$$

where $z_{ij}$ represents the j-th impedance signal sample in the i-th cardiac cycle consisting of $N_i$ samples, and m is the number of cardiac cycles.

The various sums and the minimum of signal $z_{ij}$ are defined as follows:

$$A_i^e = \sum_{j=1}^{N_i/2} z_{ij} \text{ for } i = 1, \ldots, m \text{ when } N_i \text{ is even} \quad [4]$$

$$A_i^o = \sum_{j=1}^{(N_i-1)/2} z_{ij} \text{ for } i = 1, \ldots, m \text{ when } N_i \text{ is odd} \quad [5]$$

$$T_i = \sum_{j=1}^{N_i} z_{ij} \text{ for } i = 1, \ldots, m \quad [6]$$

$$\mu_i = \min_j(z_{ij})$$

Equations [2] and [3] can be rewritten as:

$$HCA_i = \frac{A_i^e - \frac{N_i \mu_i}{2}}{T_i - N_i \mu_i} \text{ for } i = 1, \ldots, m \text{ when } N_i \text{ is even} \quad [7]$$

$$HCA_i = \frac{A_i^o - \frac{(N_i-1)\mu_i}{2}}{T_i - N_i \mu_i} \text{ for } i = 1, \ldots, m \text{ when } N_i \text{ is odd} \quad [8]$$

Figure 4:
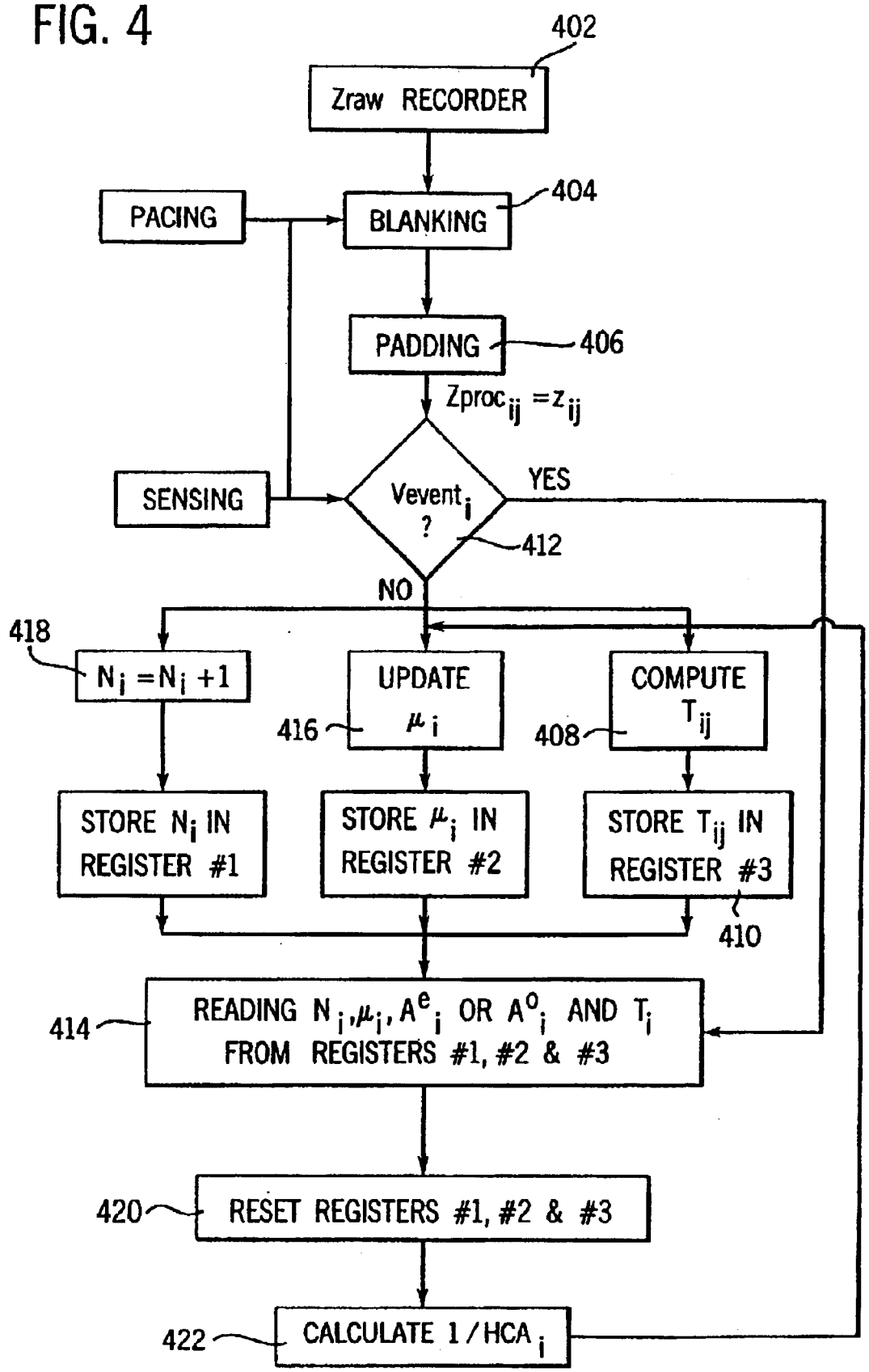
FIG. 4 is a flow chart showing a preferred embodiment of modules and processes in HCA Microprocessor 110.
Figure 5:
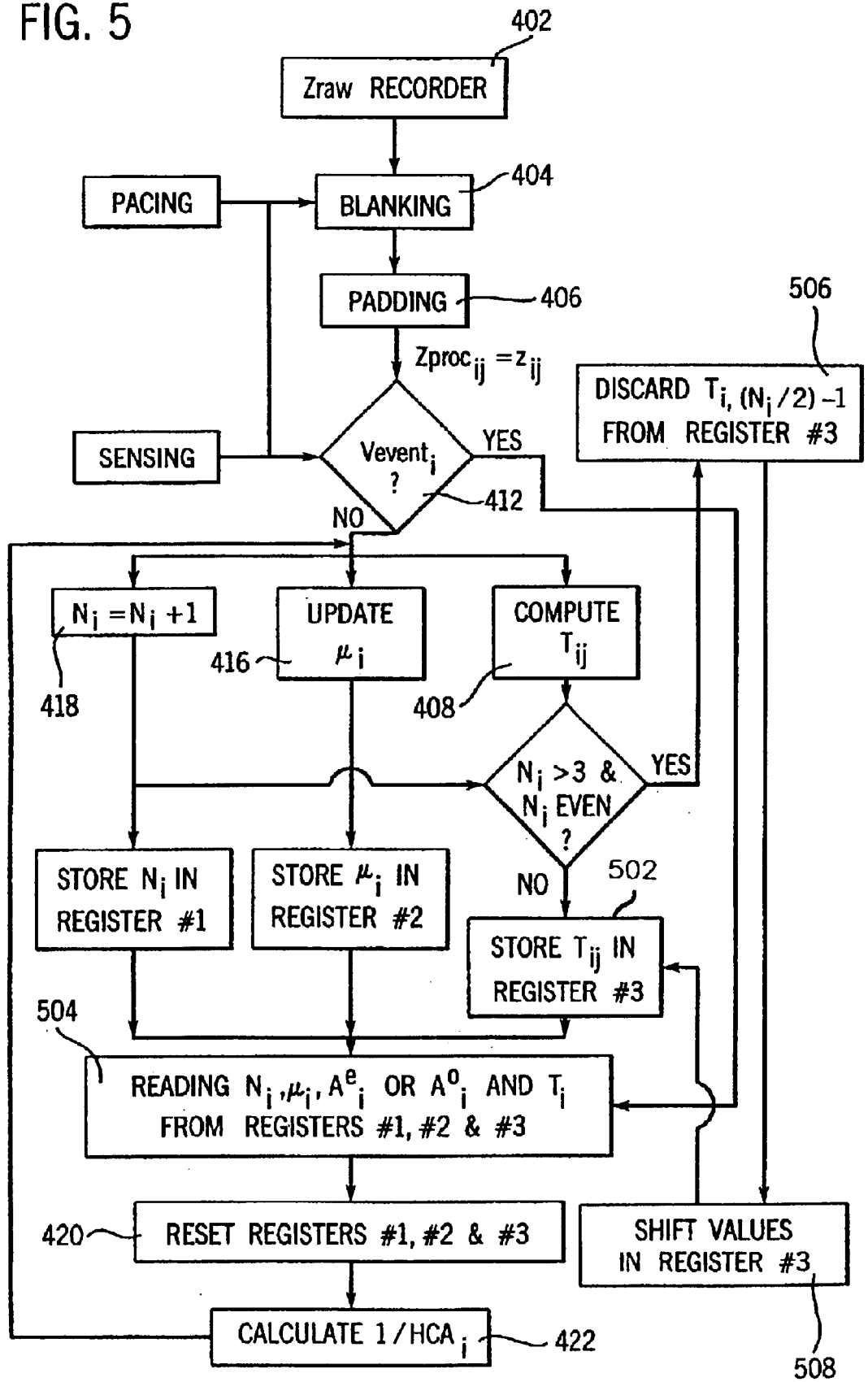
FIG. 5 is a flow chart showing an alternative preferred embodiment of modules and processes in HCA Microprocessor 110.

Either equation [7] or equation [8] is then used directly in calculating HCA values in the preferred embodiments of this invention by a 1/HCA Computing module 422 illustrated in FIGS. 4 and 5. Obtaining the values of $A_i$, $T_i$, and $\mu_i$ is critical in deriving the HCA value for each cardiac cycle. In a preferred embodiment outlined in FIG. 4, partial cumulative sums $T_{ij}$ and primitives $N_i$ and $\mu_i$ are computed in real time in Computing modules 408, 418 and 416, respectively. Connected to Computing module 408, a Storing module 410 then stores the result of each partial cumulative sum $T_{ij}$ in a register, as $Zproc_{ij}$ is being continuously entered. After the ventricular event signal (paced or sensed) determines the end of a cycle (and consequently the start of the next one) through a Cycle-End-Determining module 412, the value of $T_i$, and of $A_i^e$ or $A_i^o$ are read from the registers. This reading is done by module 414. Finally, primitives $T_i$, $N_i$, $A_i^e$ or $A_i^o$, and $\mu_i$ are used by the Computing module 422 to calculate the value of 1/$HCA_i$ according to equation [7] or [8]. In this embodiment, the size of the register is proportional to the number of samples measured per cardiac cycle. For instance, given a lower rate limit of 40 ppm (i.e., an interval of 1.5 seconds) and a sampling frequency of 50 Hz, the maximum number of samples needed for a cardiac cycle is 75. Since a 16-bit register is needed for storing the cumulative sum values, the total size of the memory needed for this purpose is thus 150 bytes.

Figure 6A:
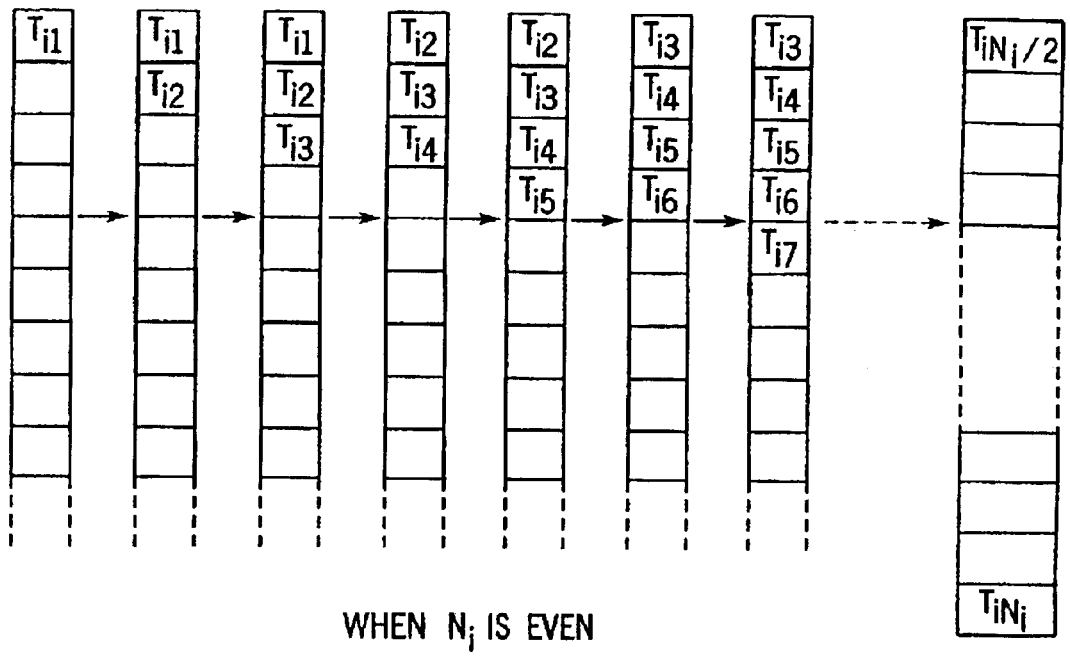
FIGS. 6(a) and 6(b) illustrate a storing and discarding mechanism of a shift register used for implementation of 1/HCA computation in HCA Microprocessor 110 in the alternative preferred embodiment of this invention.
Figure 6B:
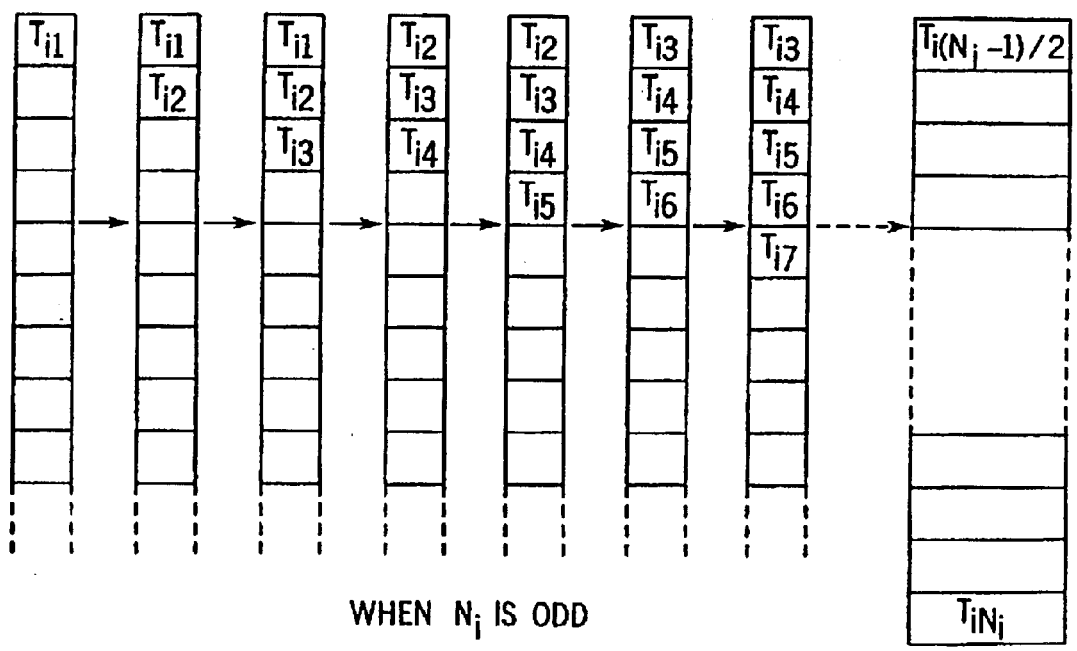

In another preferred embodiment shown in FIG. 5, partial cumulative sums $T_{ij}$ and primitives $N_i$ and $\mu_i$ are similarly computed in real time, through Computing modules 408, 418 and 416, respectively. However, instead of storing every partial cumulative sum of Zproc samples in a register, a shift register is used to allow for the previously computed cumulative sums to be discarded as new samples are recorded, which is done by a Discarding module 506. More specifically, a partial cumulative sum $T_{ij}$ is dropped from the shift register when it is no longer needed to determine either $A_i^e$ or $A_i^o$ (see equation [4]). An example of register usage is demonstrated in FIGS. 6(a) and 6(b). The size of the register is now proportional to half of the number of samples measured per cardiac cycle. Storing module 502 stores the result of a new partial cumulative sum $T_{ij}$ in the register as each new $Zproc_{ij}$ is entered (FIG. 5). When the current value of the counter 418 $N_i$ is even (and greater than 3), the shift register will perform the two following operations: discard $T_{i(Ni/2)-1}$ from the register #3 and shift one position backwards the values of register #3. These operations are performed by the Discarding module 506 and a shifting module 508. The new $T_{ij}$ is then added to the last position of the register #3. Thus, this method requires a smaller register but involves more operations of data management in the register. When the module 412 detects the end of the cardiac cycle (and consequently the start of the following one), the values of $T_i$, $A_i^e$ or $A_i^o$, $\mu_i$, and $N_i$ are read from the registers #1, #2, and #1. The value of 1/$HCA_i$ is then computed using equation [7] or [8]. Using the same example as in the first preferred embodiment, the total size of the register memory needed here is only 75 bytes at the same sampling rate.

As described above, HCA presents two features according to the embodiment of the present invention. First, HCA affords a strong correlation with workload at slow to normal heart rate, and is consequently a good parameter to trigger the increase in hemodynamically driven pacing rate or to limit the decrease of driven pacing rate advised by another sensor such as an accelerometer. Hence, HCA identifies a Hemodynamic Lower Rate Limit (HLRL). Second, HCA provides hemodynamic feedback information at a fast heart rate. It detects a hemodynamic compromise state. In responding to another sensor such as an accelerometer or in responding to a supraventricular tachycardia, HCA signifies the maximum tolerated rate. Therefore, a Hemodynamic Upper Rate Limit (HURL) can be defined by HCA at high heart rates.

To elaborate on these two critical elements of HCA, data from several episodes of an anesthetized dog at well-tolerated and not-well-tolerated pacing rates in Experiments I, II, III and IV were obtained as follows:

EXPERIMENT I

Correlation Between 1/HCA and Workload: Without Dobutamine

Figure 7E:
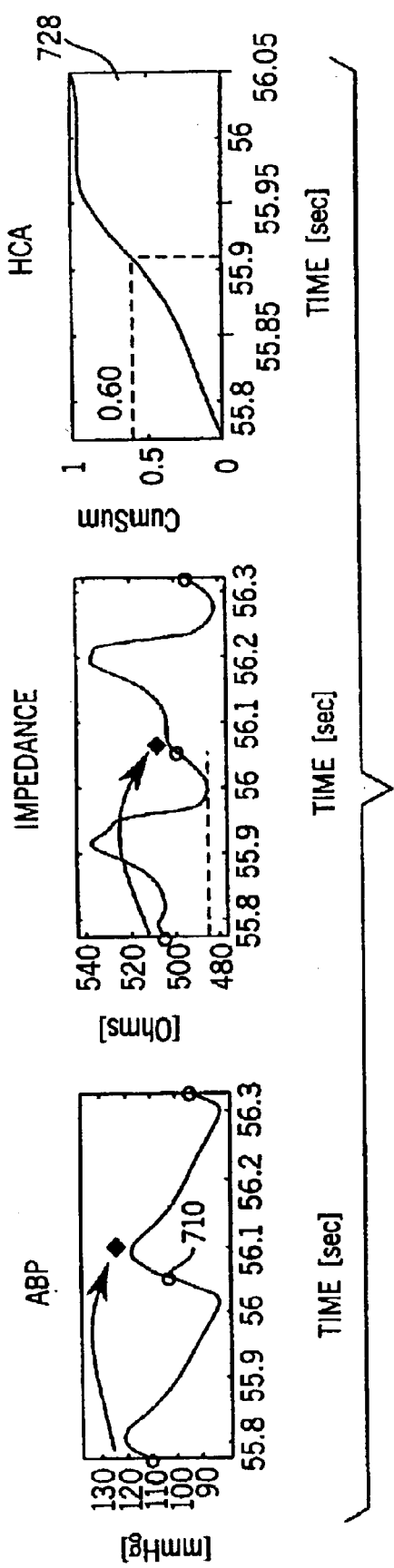
Figure 8C:
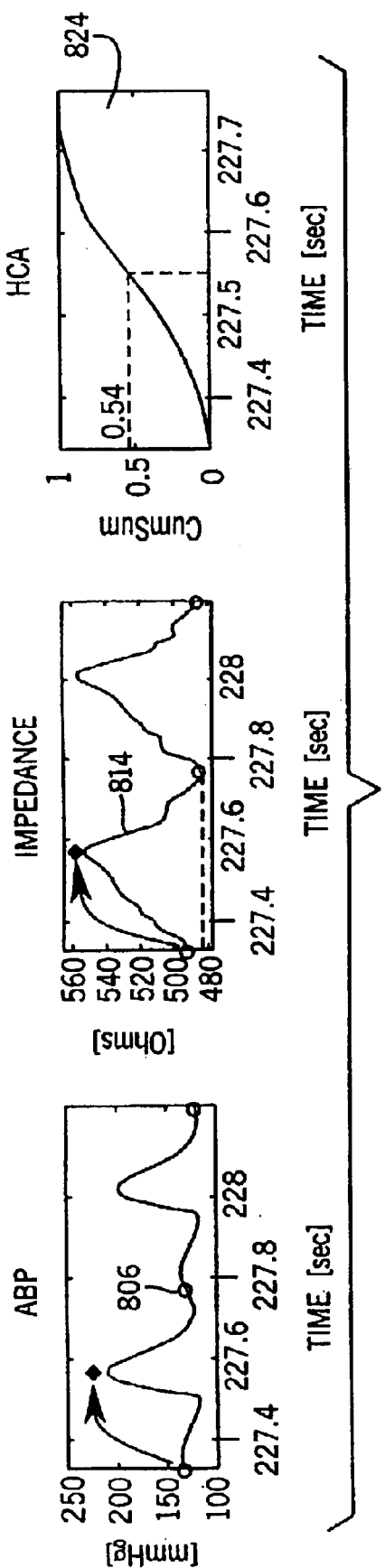
Figure 8D:
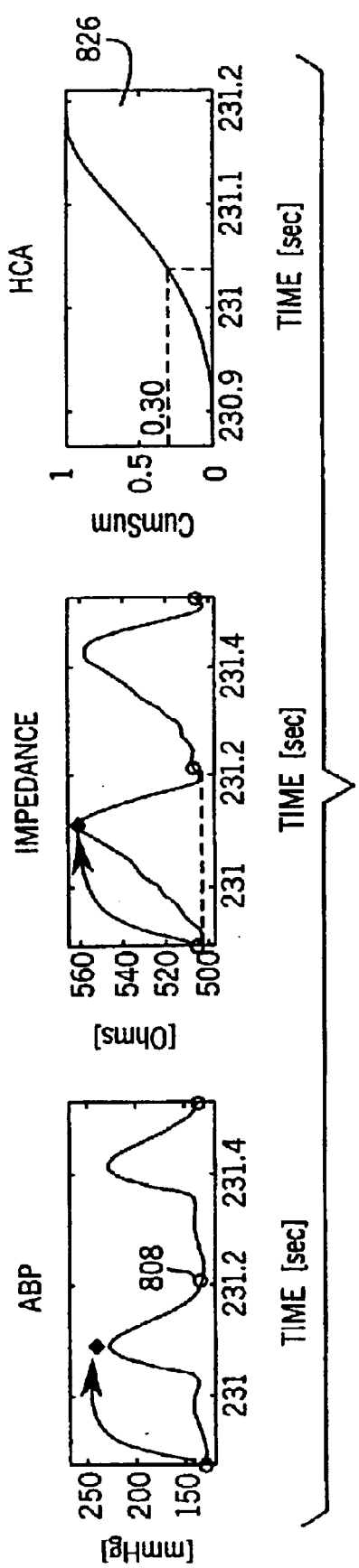
Figure 8E:
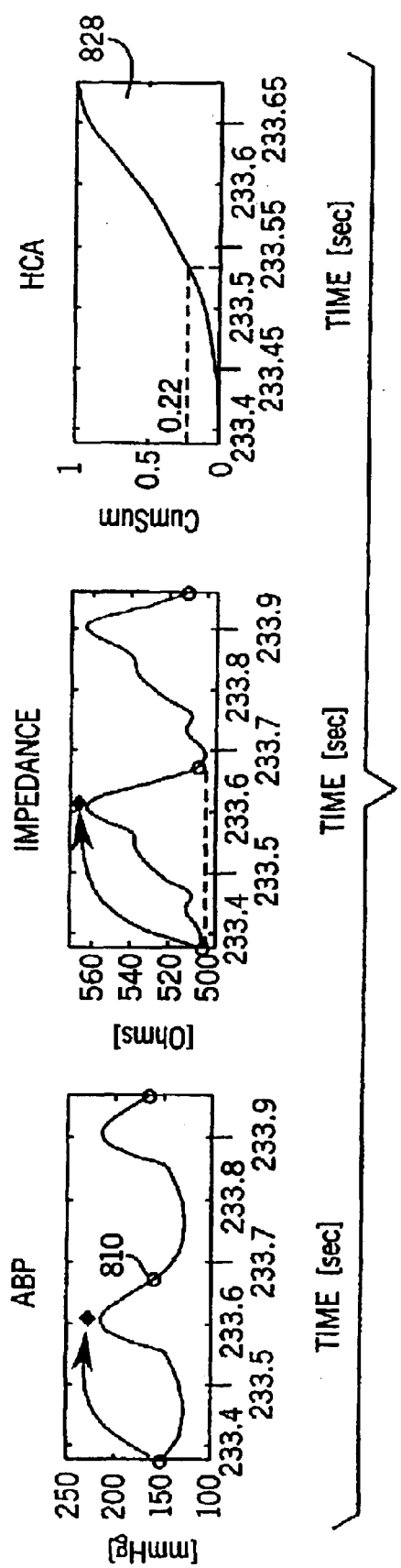

FIGS. 7(a) to 7(e) show the evolution over time of the peripheral ABP (artery blood pressure) and the impedance waveforms while the dog was paced at different ventricular rates: 65 ppm in FIG. 7(a), 105 ppm in FIG. 7(b), 134 ppm in FIG. 7(c), 165 ppm in FIG. 7(d), and 204 ppm in FIG. 7(e), without the use of any catecholamine. ABP waveforms and intracardiac impedance waveforms for two cardiac cycles along with the plots for HCA computation for the first cardiac cycle are shown in each of these figures. There is a progressive shift of the ABP waveform with respect to the pacing spikes (cardiac electrical activity) as the pacing rate increases, such that the following spike occurs while the ABP waveform shows an incomplete cardiac relaxation (compare points 702, 704, 706, 708 and 710). This progressive shift is also manifested in the intracardiac impedance waveforms. The higher the pacing rate is, the wider the impedance waveform is (compare waveforms 712 and 714), or equivalently the longer the total ventricular active time is (U.S. Pat. No. 5,235,976). This shift can also be viewed as the "climbing" of the ventricular event indicating the start of a cardiac cycle along the impedance waveform of the previous cardiac cycle. The result of such a progressive shift is that the subsequent spike, and hence the subsequent systole, occurs before the impedance waveform shows a complete cardiac relaxation (compare waveforms 712 and 714). Therefore, the hemodynamic compromise is demonstrated by the relatively long ventricular active time leading to the shortening of the diastolic or filling time.

When the pacing rates are well tolerated, the HCA value decreases as the ventricular rate (Vrate) increases, as shown by curves 720, 722 and 724, comparatively. The maximum of the ABP waveform increases with the increase in pacing rate. In order to have a positive correlation with the ABP evolution, usually the inverse of HCA (1/HCA) is used as the monitoring parameter for hemodynamics. When the hemodynamic status of the dog is compromised at high ventricular rates, as shown in FIGS. 7(d) and 7(e), the maximum of the ABP waveform decreases at increasing pacing rates. The HCA value increases (thus 1/HCA value decreases) with the pacing rate (compare curves 726 and 728), indicating the presence of a hemodynamic compromise state.

EXPERIMENT II

Correlation Between 1/HCA and Workload: With Dobutamine

Parallel with the data in FIGS. 7(a)–7(e), evolution of the ABP waveform and the impedance waveform recorded while the dog was being paced at corresponding pacing rates after dobutamine injection is shown in FIGS. 8(a)–8(e). Inotrope positive effect of dobutamine leads to a relatively shortened systole. The ventricular active time is shortened and thus the ABP waveform comes back to the baseline level before the occurrence of the next pacing spike (compare points 802, 804, 806, 808 and 810), so does the impedance waveform (compare waveforms 812 and 814), since the shift of the impedance waveform is also substantially reduced. The effect of dobutamine is also reflected by the continuous decrease of HCA values (hence increase of 1/HCA values) as the pacing rate increases (compare curves 820, 822, 824, 826 and 828). No hemodynamic compromise is encountered in this situation.

It is important to note from both FIGS. 7(a)–7(e) and 8(a)–8(e) that the impedance waveforms recorded at well-tolerated pacing rates are clearly distinguishable from the ones recorded at not-well-tolerated pacing rates. Therefore, as discussed above, the HCA parameter effectively characterizes the morphology of the impedance waveform to differentiate between the different hemodynamic states of a patient, according to the preferred embodiment of this invention.

EXPERIMENT III

Detect a Metabolic Demand at Slow Heart Rates Using 1/HCA

Figure 9A:
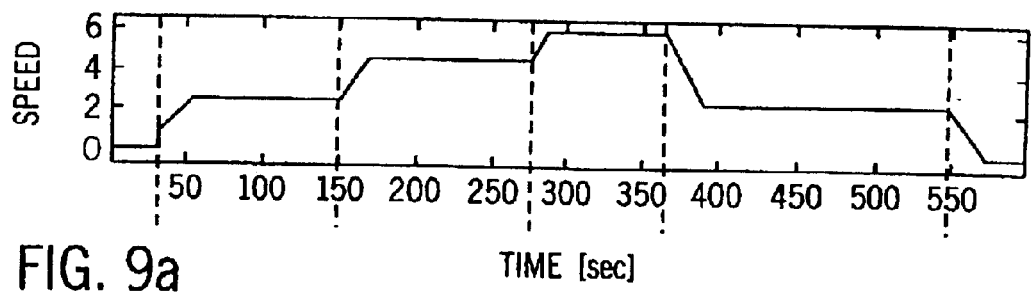
FIGS. 9(a)–9(d) are illustrations of (a) the treadmill speed, (b) ventricular rate, (c) atrial rate, and (d) 1/HCA value from an ambulatory dog performing an exercise on a treadmill.
Figure 9B:
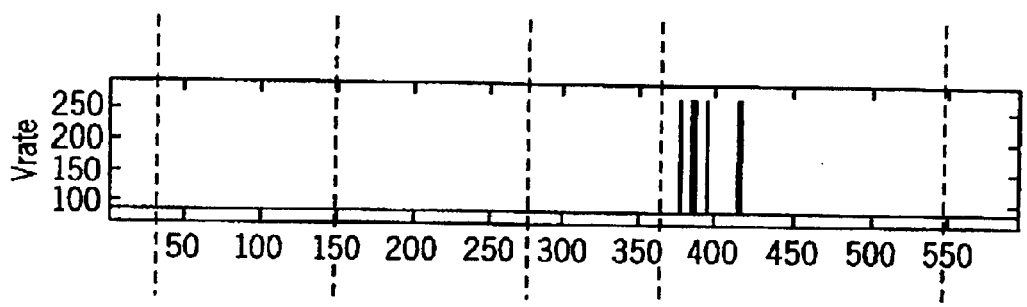
Figure 9C:
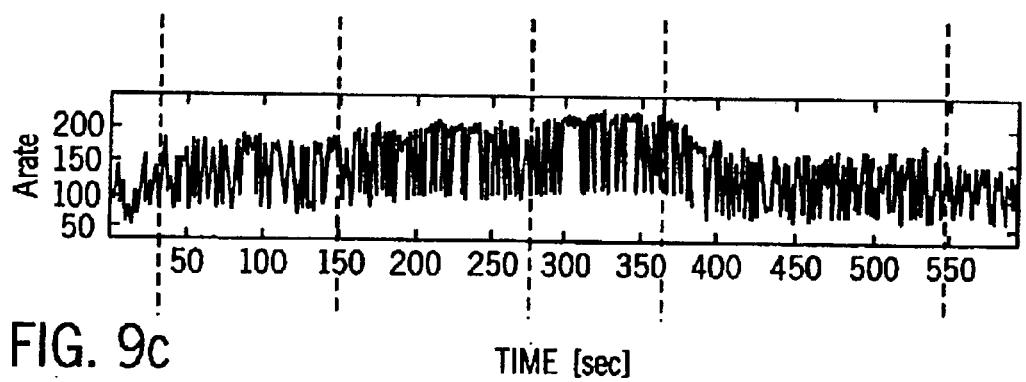
Figure 9D:
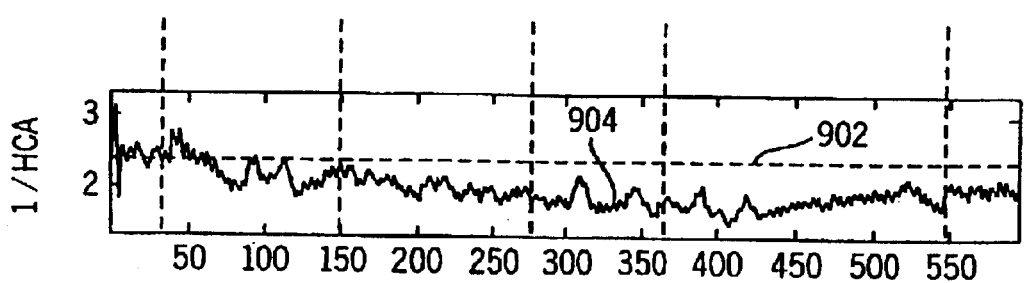

To further illustrate the correlation between 1/HCA and metabolic demands at a slow heart rate, the example in FIGS. 9(a)–9(d) shows an episode recorded on an AV node ablated dog performing a treadmill exercise while maintaining the VVI pacing rate at 85 ppm. In this experiment, bradypacing leads were used. The speed of the treadmill and the ventricular rate are shown respectively in FIGS. 9(a) and 9(b). The ventricular rate (V rate) is defined as the number of ventricular depolarizations per minute, expressed as ppm. The faster the treadmill operates, the higher the metabolic demand is and the higher the atrial rate is, as shown in FIG. 9(c). The atrial rate (Arate), which is defined by the number of atrial depolarizations per minute, expressed as ppm, reflects the physiologic response of the sinus node to the increasing metabolic demand. Importantly, the higher the speed of the treadmill, the lower the value of 1/HCA, as shown by the dashed line 902 and the 1/HCA curve 904 in FIG. 9(d). Therefore, 1/HCA determines whether or not the heart rate is too low for a given workload.

EXPERIMENT IV

Detect the Hemodynamic Compromise State Using 1/HCA

Figure 10A:
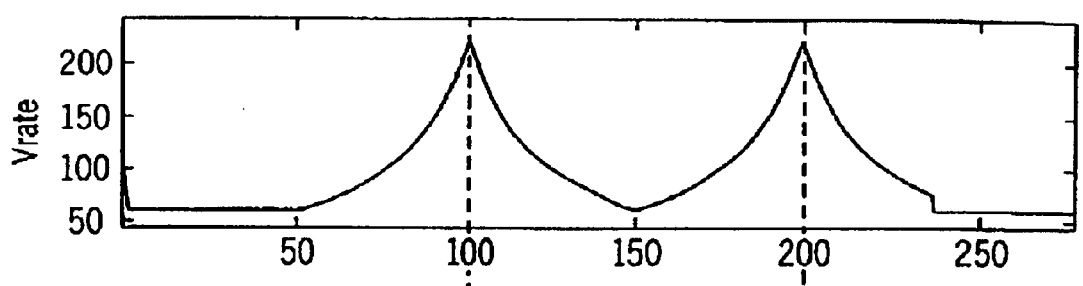
FIGS. 10(a)–10(c) are illustrations of (a) the ventricular rate, (b) 1/HCA value, and (c) maximum, mean and minimum of ABP.
Figure 10B:
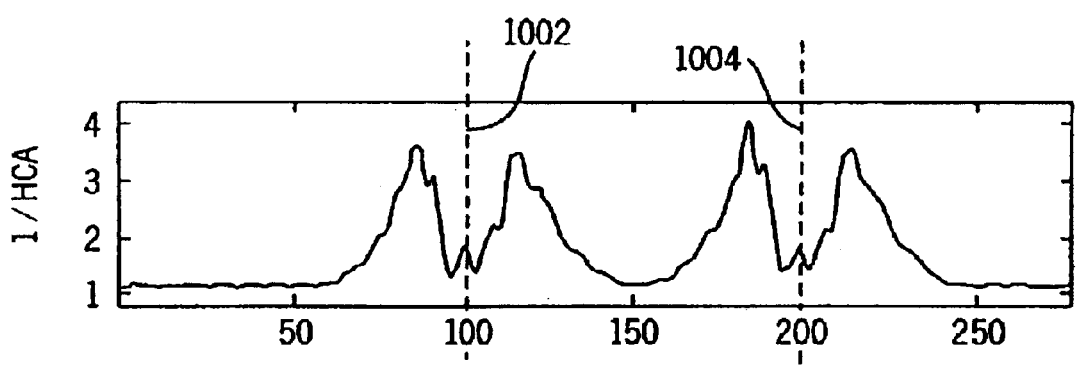
Figure 10C:
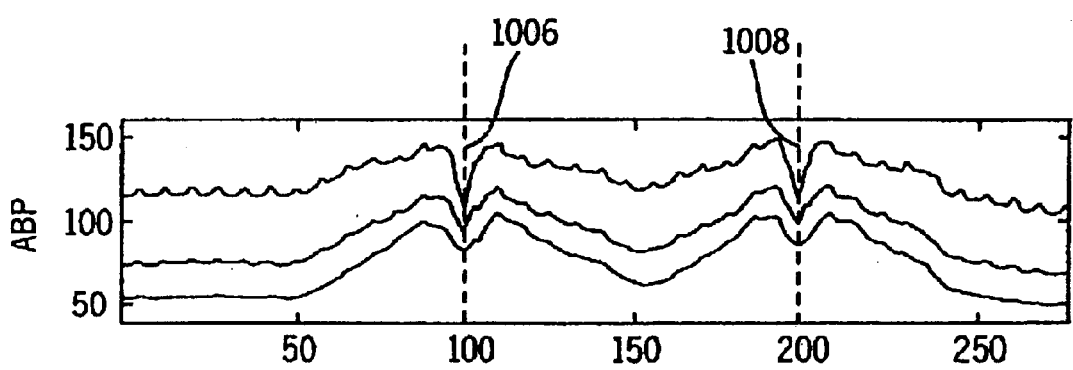

Referring to FIGS. 10(a) to 10(c), details of the detection of hemodynamic compromise by 1/HCA are elaborated. In this experiment, an anaesthetized dog was paced following continuous DDD pacing ramps from 60 to 240 ppm and back again, occurring every 100 seconds. The dog's physiologic condition remains unchanged at baseline. Bradypacing leads were used in this experiment. The peripheral ABP shown in FIG. 10(c) demonstrates a clear dip at the highest pacing rates (see points 1006 and 1008), indicating the presence of hemodynamic compromise. The inappropriate fast pacing rate without any physiologic demand is also manifested by the decrease in 1/HCA values (see points 1002, 1004). Therefore, 1/HCA is a good indicator for hemodynamic compromise states, hence setting a HURL.

An additional example is provided in Experiment V below to illustrate the correlation of 1/HCA with hemodynamics of the tested animal paced with dobutamine injections.

EXPERIMENT V
Monitor Hemodynamics After Dobutamine Injection Using 1/HCA

Figure 11A:
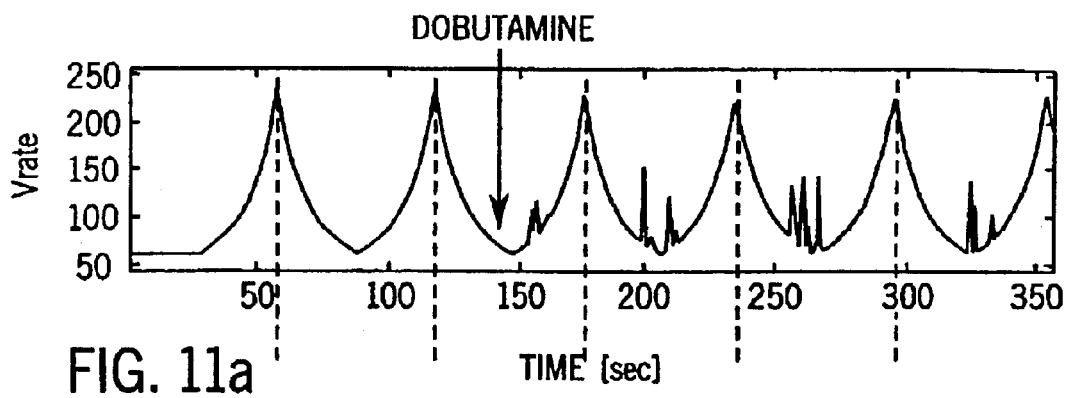
FIGS. 11(a)–11(c) are illustrations of (a) the ventricular rate, (b) 1/HCA value, and (c) maximum, mean and minimum of ABP recorded at ascending and descending pacing rate ramps.

An anesthetized dog was paced in DDD mode following continuous pacing ramps from 60 to 240 ppm at every 60 seconds. Dobutamine was injected after two entire pacing ramps at the time point 140 second as shown in FIG. 11(a). A hemodynamic compromise is observed during fast pacing rates without dobutamine at the time points 55 second (point 1102) and 115 second (point 1104), according to the peripheral Artery Blood Pressure information in FIG. 11(c). After dobutamine injection, however, the highest pacing rates create little or no decrease in blood pressure at the time points 175 second (point 1106), 235 second (point 1108), 295 second (point 1110) and 355 second (point 1130).

Figure 11B:
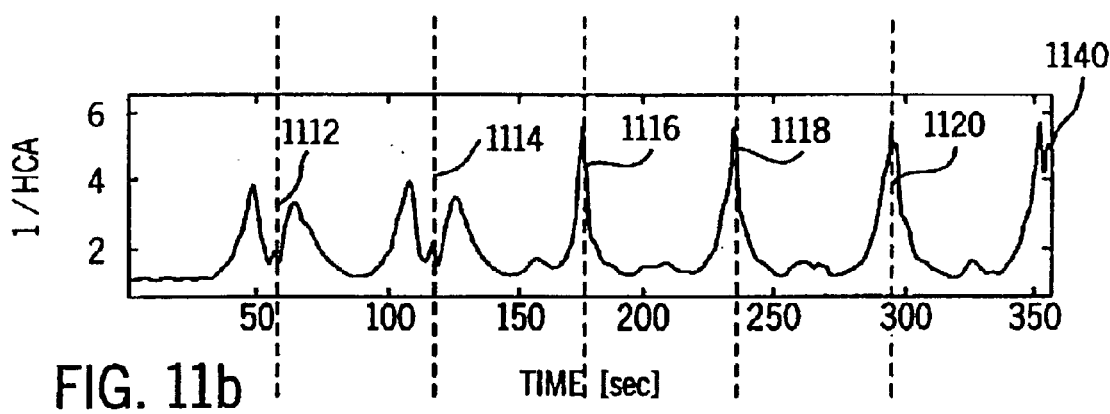
Figure 11C:
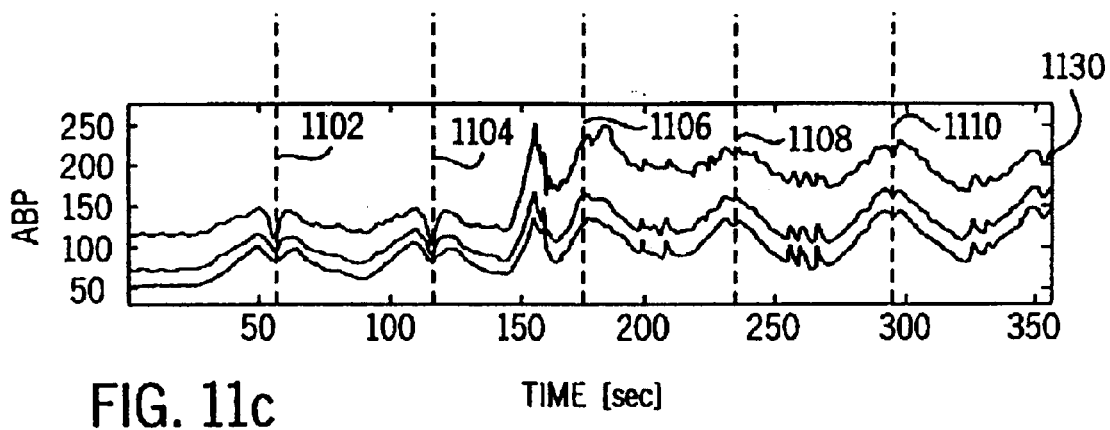

FIG. 11(b) demonstrates that the 1/HCA parameter follows an evolution parallel to that of the hemodynamics of the tested animal, shown in FIG. 11(c). Specifically, the 1/HCA parameter shows a decrease that is concomitant to the decrease in peripheral Artery Blood Pressure (ABP).

Good hemodynamic tolerance of fast pacing rates after dobutamine injection is evident in ABP's evolution (comparing points 1102 and 1104 with points 1106 and 1108). Correspondingly, the 1/HCA parameter no longer presents a decrease at the highest pacing rates during this post-dobutamine injection period (comparing points 1112 and 1114 with points 1116 and 1118).

It is to be noted that dobutamine was injected in a single shot and was progressively washed out. This is reflected in a slight decrease in the ABP at the highest pacing rates of the two last pacing ramps, indicating a slight hemodynamic compromise at the time points 295 second (point 1110) and 355 second (1130). Accordingly, the 1/HCA parameter also presents a slight decrease at those high pacing rates (points 1120 and 1140).

This experiment, therefore, provides additional confirmation of the ability to use 1/HCA to monitor accurately hemodynamic states.

As shown in FIG. 1, the intracardiac impedance parameter HCA enables a closed-loop sensing and responding mechanism in a cardiac activity management device. An increase in driven pacing rate, for instance, can be interrupted when an incremental increase in rate leads to a decrease in 1/HCA value, which signifies a hemodynamic compromise state, hence HURL. On the other hand, when 1/HCA continues to increase as the physical demand increases, an increase of hemodynamically driven pacing rate should be invoked. Meanwhile, the decrease of driven pacing rate advised by another sensor, such as an accelerometer, should be limited when the 1/HCA curve presents deep dips, which signify HLRL. Therefore, a Hemodynamic Pacing Range (HPR) can be defined as the range bound by HURL and HLRL. The determination of an HPR thus allows a closed-loop control of the driven pacing rate of an implantable pacemaker in a preferred embodiment of this invention. An example of HURL and HLRL identification is illustrated in Experiment VI below according to the preferred embodiment of this invention.

EXPERIMENT VI
Determine HURL and HLRL Using 1/HCA

Referring to FIGS. 12(a)–12(d), this episode was recorded in an AV node ablated dog engaged in a treadmill exercise. To simulate the behavior of an accelerometer, the dog was paced at continuous pacing ramps from 80 to 170 ppm and back again at every 60 seconds. The treadmill did not move and the dog stood still at the first two pacing ramps. The speed of the treadmill and the ventricular rate are recorded in FIGS. 12(a) and 12(b), respectively. The faster the treadmill operates, the higher the metabolic demand is, and the higher the atrial rate is (note the elevating trend of curve 1220), since the atrial rate reflects the physiologic response of the sinus node to the increasing metabolic demand.

It can be observed on 1/HCA curve 1230 that the higher the metabolic demand is, the deeper and the wider the dips are at low pacing rates (e.g., compare the dips covering points 1232, 1234, and 1236). This indicates that the pacing rate is not sufficient to the workload imposed by the speed of the treadmill. To determine an HLRL, we identify the decreasing point on each dip on 1/HCA curve 1230 that corresponds to a descending ramp of Vrate (e.g., points 1232, 1234, and 1236). A vertical dashed line is then drawn from each of these points which intersects with the overlaid Vrate plot in FIG. 12(b) at points 1212, 1214, and 1216, respectively. Connecting these points (e.g., 1212, 1214, and 1216), line 1210 representing the HLRL is generated.

In contrast, the higher the metabolic demand is, the smaller the dips are at high pacing rates on 1/HCA curve 1230 (e.g., compare the dips covering points 1233, 1235, and 1237). This indicates that an inappropriate high pacing rate results in a hemodynamic compromise status when the metabolic demand is low, while a high pacing rate results in no or little hemodynamic compromise status when the metabolic demand increases. To determine a HURL, the decreasing point on each dip on 1/HCA curve 1230 that corresponds to an ascending ramp of Vrate (e.g. points 1233, 1235, and 1237) is identified. A vertical dashed line is then drawn from each of these points which intersects with the overlaid Vrate plot in FIG. 12(b) at points 1213, 1215, and 1217 respectively. Connecting these points (e.g. 1213, 1215, and 1217), line 1218 representing the HURL is generated.

A second example of HURL and HLRL determination is provided in Experiment VII below.

EXPERIMENT VII
Determine HURL and HLRL Using 1/HCA

Figure 13A:
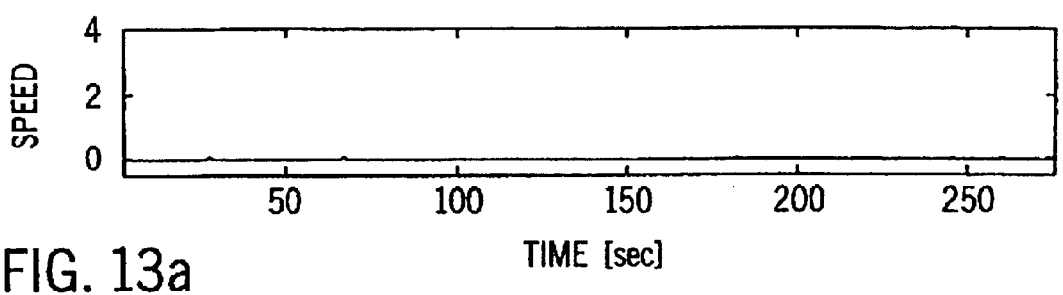
FIGS. 13(a)–13(d) are overlaid plots of the changes over time in several cardiac cycles in (a) the treadmill speed, (b) ventricular rate, (c) atrial rate and (d) 1/HCA value in an ambulatory dog recovering from an exercise on a treadmill, demonstrating HURL and HLRL determination.
Figure 13B:
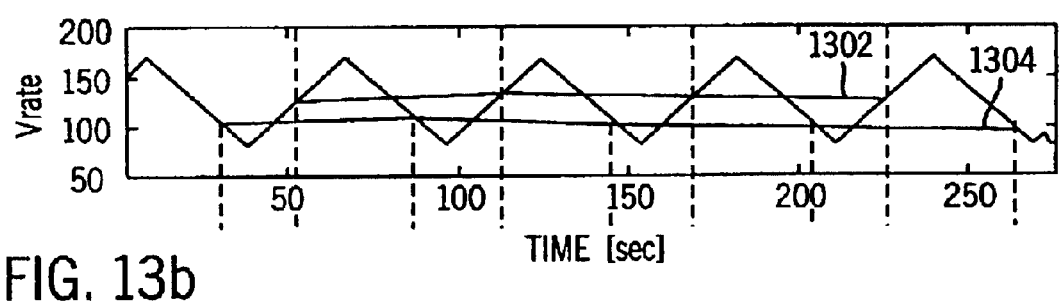
Figure 13C:
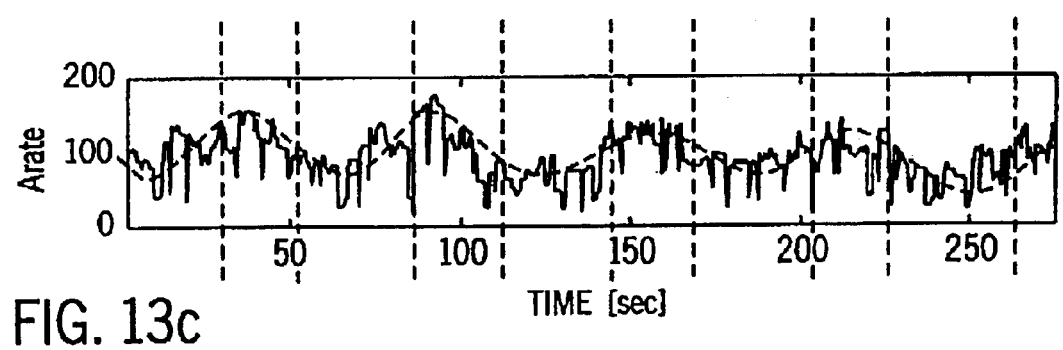
Figure 13D:
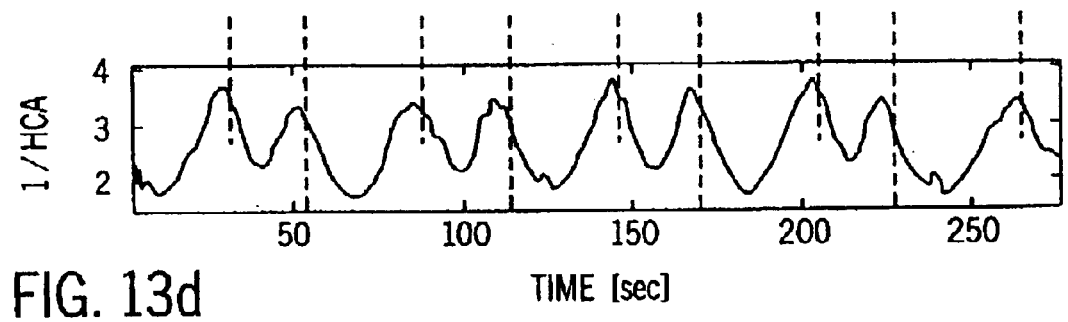
Figure 14A:
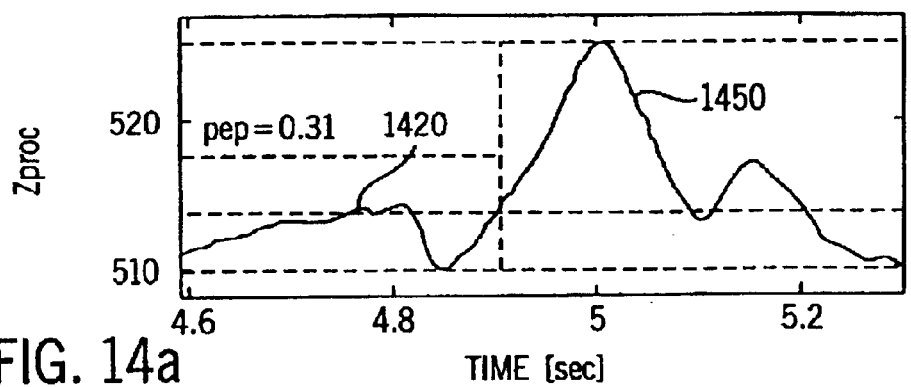
FIGS. 14(a)–14(h) are illustrations of impedance waveforms and the corresponding plots for 1/HCA computation in right and left panels, respectively, through several cardiac cycles.
Figure 14B:
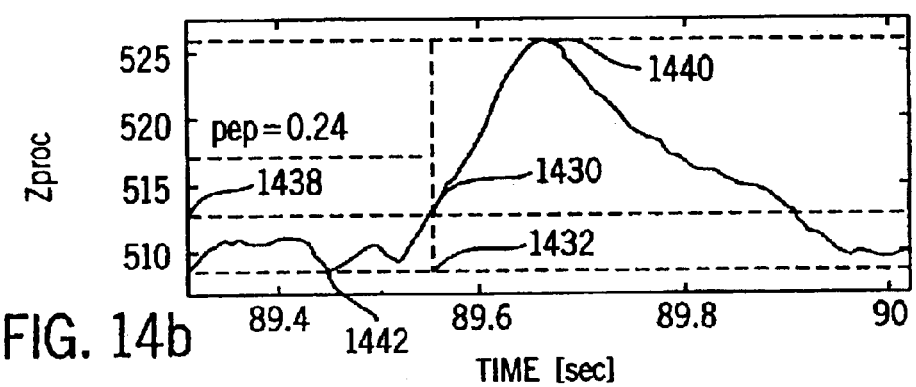
Figure 14C:
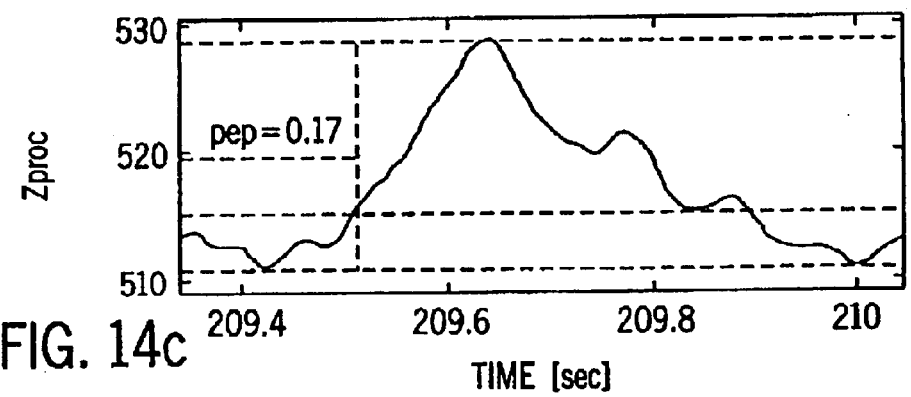
Figure 14D:
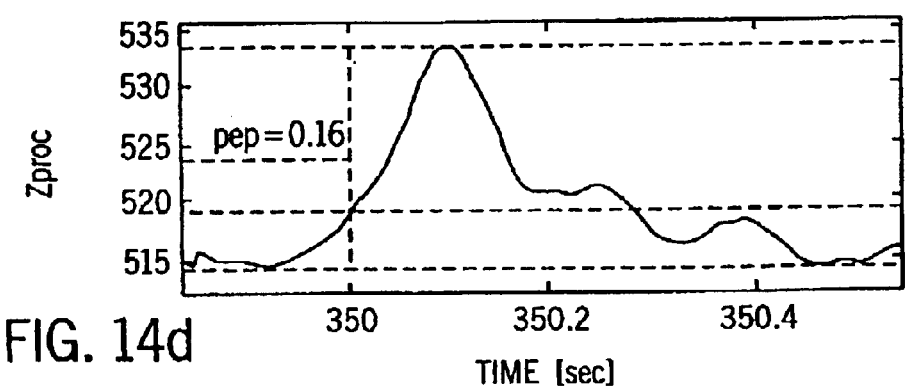
Figure 14E:
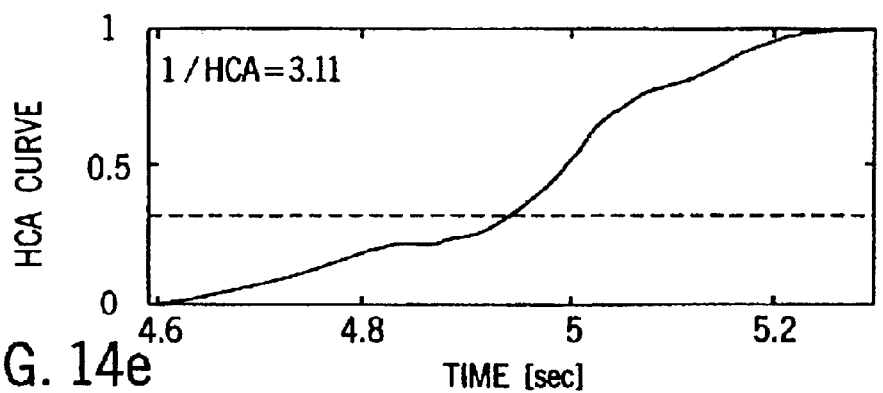
Figure 14F:
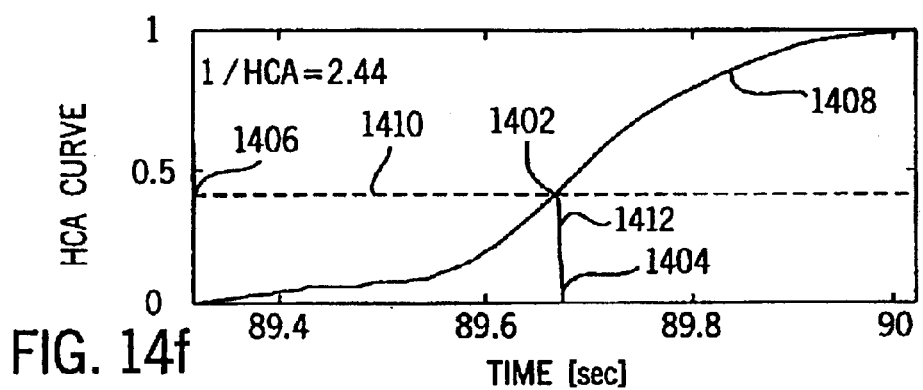
Figure 14G:
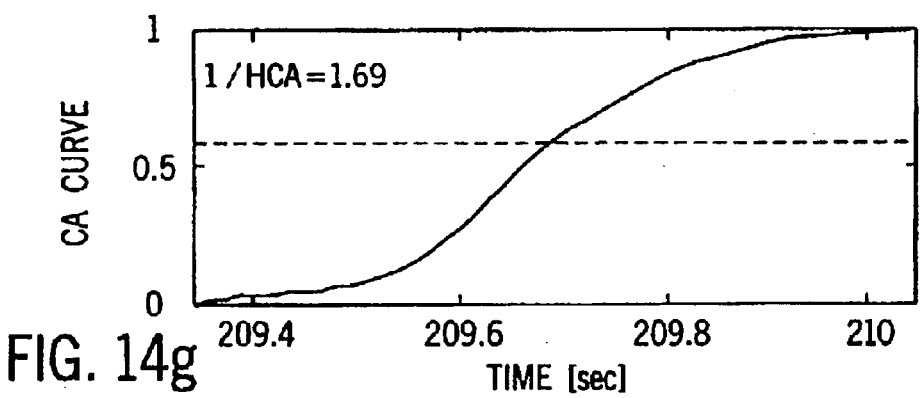
Figure 14H:
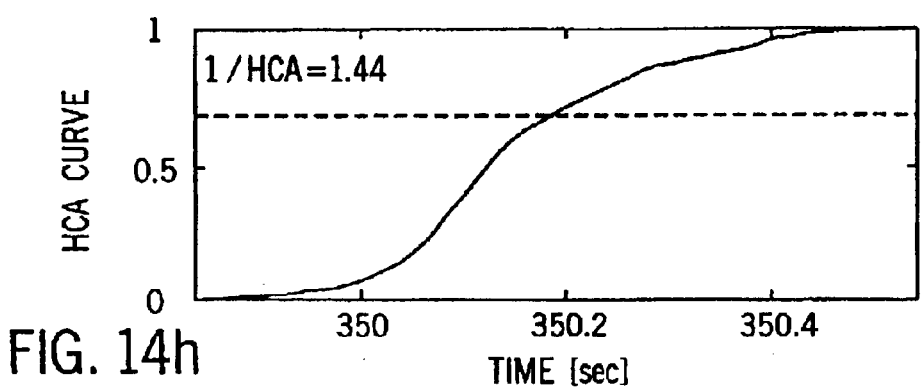

Referring to FIGS. 13(a)–13(d), this episode is a continuation of the previous one, the ambulatory dog is paced in VVI mode following continuous pacing ramps from 80 to 170 ppm while recovering from the treadmill exercise. A two-terminal configuration (RVtip to RVring) was used in this experiment. As shown in FIG. 13(a), the treadmill was stopped. The atrial rate in FIG. 13(c) shows a profile that is the mirror image of the ventricular pacing rate in FIG. 13(b), which indicates that the highest pacing rates are too fast for the current metabolic demand, while the lowest pacing rates are too slow for it.

Figure 12A:
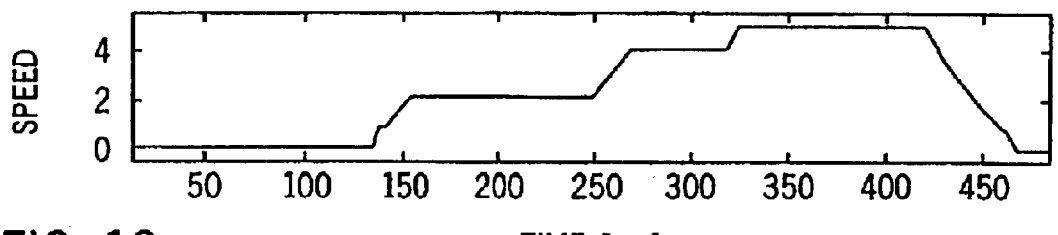
FIGS. 12(a)–12(d) are overlaid plots of the changes over time in several cardiac cycles in (a) the treadmill speed, (b) ventricular rate, (c) atrial rate and (d) 1/HCA value in an ambulatory dog engaged in an exercise on a treadmill, demonstrating HURL and HLRL determination.
Figure 12B:
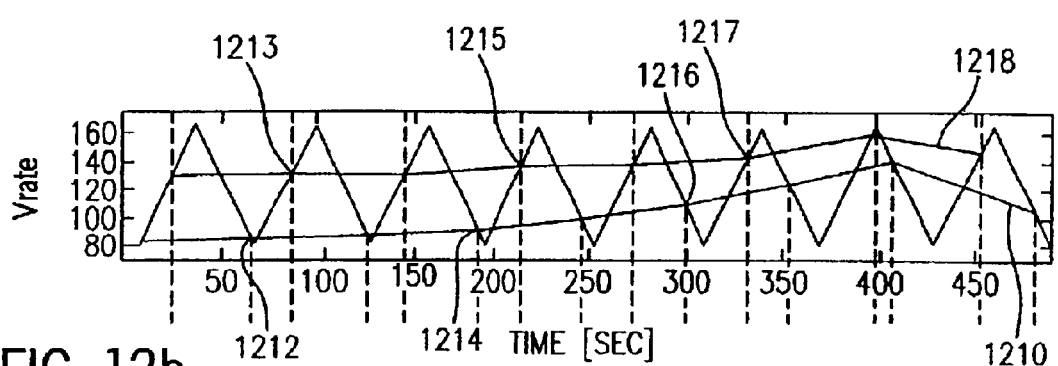
Figure 12C:
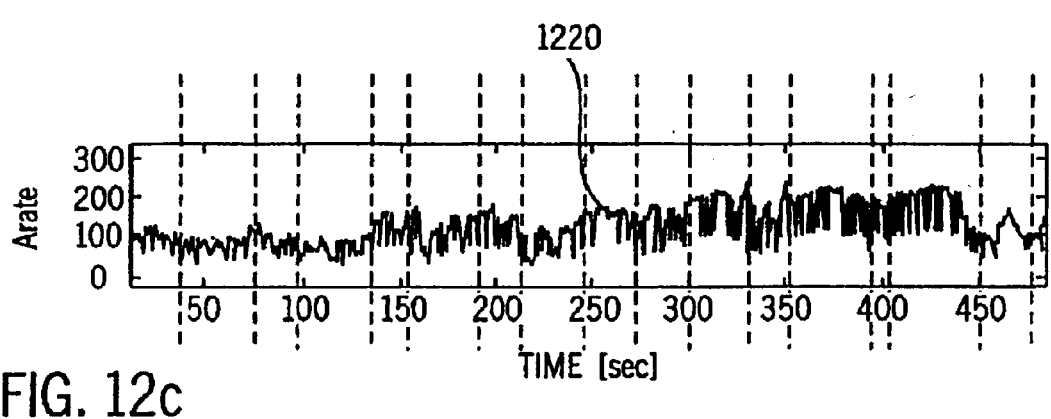
Figure 12D:
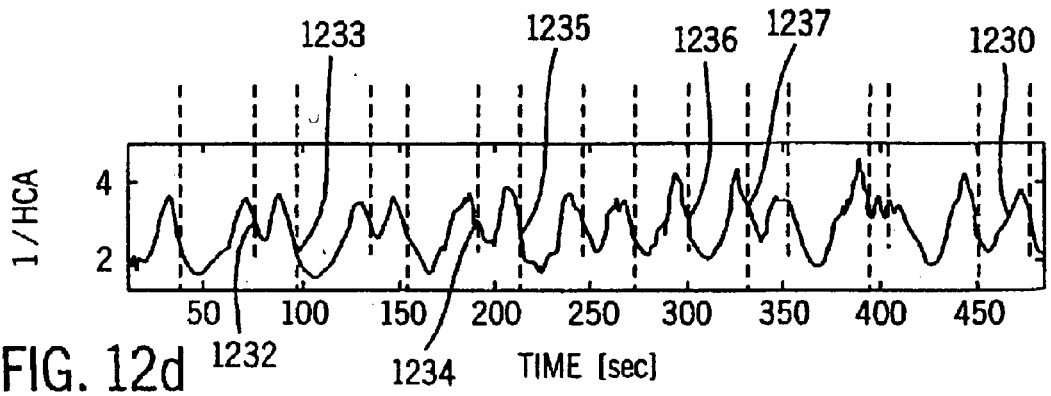

The pacing rate curve 1302 (HURL) and the pacing rate curve (HLRL) 1304 in FIG. 13(b) are drawn using the same method as the curves 1202 and 1204, respectively, in FIG. 12(b). The two curves 1302 and 1304 identify a pacing rate range between 100 ppm and 130 ppm, which encompasses the average atrial rate of 110 ppm as shown in FIG. 13(c). Thus, the HURL and HLRL identified based on 1/HCA reliably reflects the intrinsic hemodynamic status according to the preferred embodiment of this invention.

Aside from the two main features discussed above, HCA presents additional characteristics according to the preferred embodiment of this invention. Experiments VIII, IX, X, and XI discuss these aspects in detail.

EXPERIMENT VIII
HCA's Resistance to Noise and Artifacts

Figure 3C:
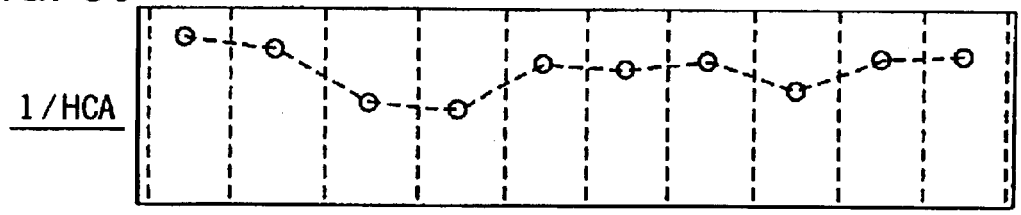

Since HCA is derived from the whole cardiac cycle rather than from localized points in an impedance waveform, it is a much more robust measurement than known intracardiac impedance derived parameters. That is, HCA is not significantly affected by noise, artifacts and multiple impedance humps. It is useful to compare HCA with Pre-Ejection Time (PEP) (U.S. Pat. No. 4,773,401) in this regard. PEP is defined as the time between the spike (electrical activity) and the beginning of the Artery Blood Pressure (ABP) waveform (mechanical activity). FIGS. 14(a)–(h) illustrate several episodes collected from an AV node ablated dog performing a treadmill test. The VVI pacing rate was maintained at 85 ppm while the dog exercised on the treadmill at a progressively increasing speed: 0 mph in FIGS. 14(a) and 14(e), 3 mph in FIGS. 14(b) and 14(f), 5 mph in FIGS. 14(c) and 14(g), and 6 mph in FIGS. 14(d) and 14(h). An impedance waveform is shown in the left panels (14(a)–14(d)) at each speed, and the area underneath the impedance waveform is plotted against time in a cardiac cycle for each speed in the right panels (14(e)–14(h)). The value of HCA at each speed is the Y coordinate of the point on each left panel curve corresponding to the mid time point of the cardiac cycle. For example, in FIG. 14(f), the mid point of the cardiac cycle is 1404, a vertical line 1412 drawn from it intersects with curve 1408 at point 1402. A horizontal line 1410 intersects with point 1402, as well as the Y axis at point 1406. Hence, the inverse of the value of point 1406 is 1/HCA. On the other hand, PEP is calculated as the duration between the ventricular electrical signal and the time when the impedance reaches 25% of the peak impedance signal. However, the detection of the start of the ventricular contraction could be error-prone. Using FIG. 14(b) as an example, the global maximum of the waveform is identified at point 1440, the minimum at point 1442. Point 1438 represents 25% of the maximum signal. Point 1430 on the curve corresponds horizontally to 1438; therefore, its X coordinate value is the value of PEP, which is read from point 1432. Note that the occurrence of the shoulder 1420 on the waveform 1450, i.e. the waveform in FIG. 14(a), can lead to an incorrect PEP value. Thus, the HCA is a more stable and accurate reflection of the hemodynamic status. The analysis of HCA and PEP in FIGS. 14(a) to (h) demonstrates that the faster the treadmill operates, the higher the metabolic demand is, the shorter the PEP is, and the lower the value of 1/HCA is.

EXPERIMENT IX

HCA's Robustness at Low Sampling Frequency

Figure 15A:
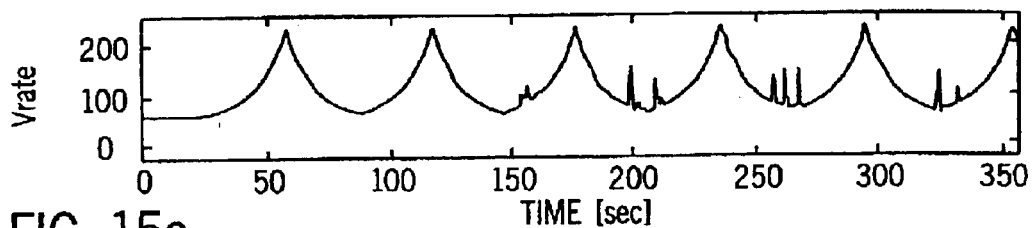
FIGS. 15(a)–(f) show the pattern of ventricular rate (Vrate), Artery Blood Pressure (ABP) and 1/HCA value calculated at different sampling frequencies.
Figure 15B:
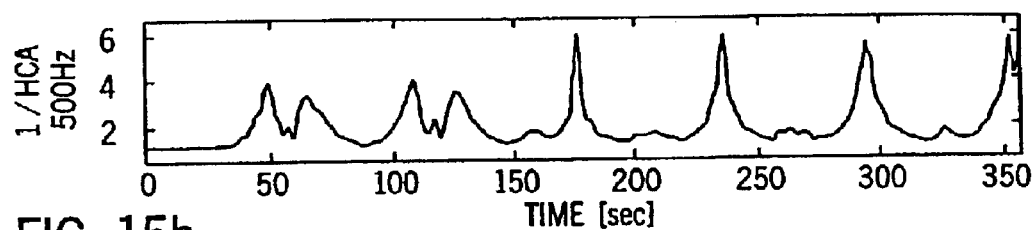
Figure 15C:
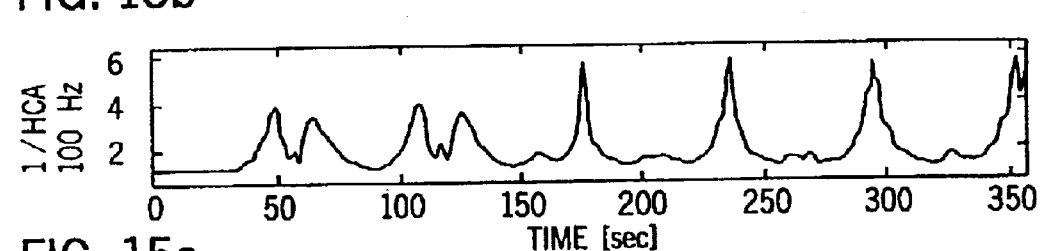
Figure 15D:
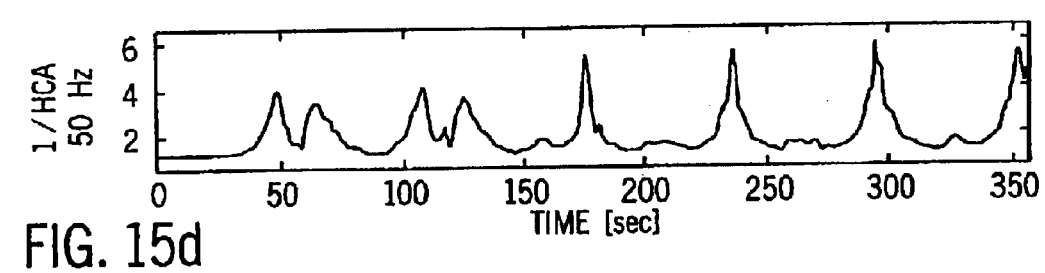
Figure 15E:
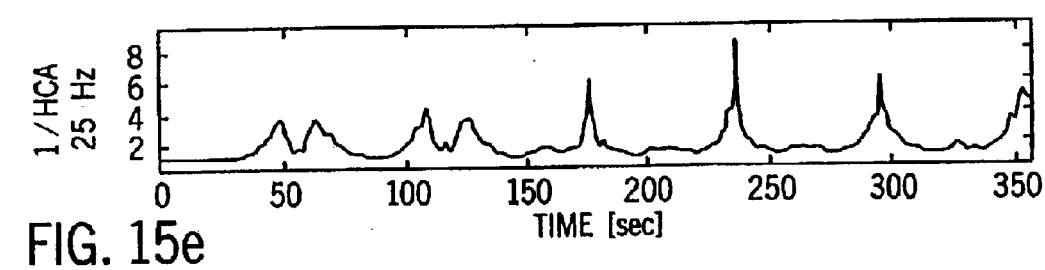
Figure 15F:
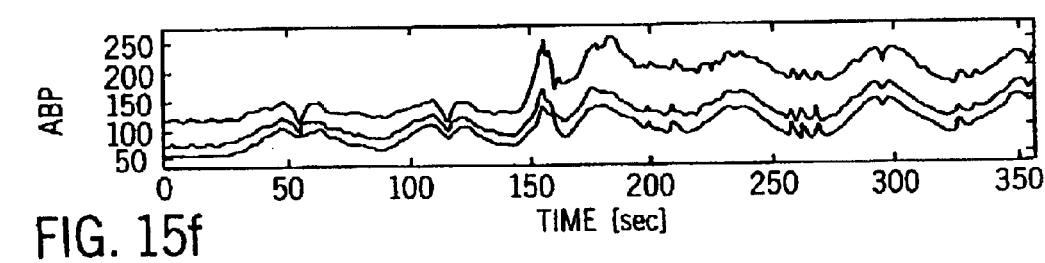

Because the calculation of HCA uses the area under an impedance waveform, the shape of this waveform dictates the result. Therefore, a lower sampling frequency would not significantly affect the accuracy and the reliability of the parameter in so far as the waveform maintains its characteristic morphology. This feature is demonstrated in FIGS. 15(b)–15(e). The episodes recorded consist of continuous pacing ramps from 60 to 240 ppm and back again occurring every 60 seconds in an anesthetized dog (FIG. 15(a)). Dobutamine is injected after the first two entire pacing ramps at the time point 140 seconds. The value of 1/HCA is calculated at a sampling frequency of 500 Hz in 15(b), 100 Hz in 15(c), 50 Hz in 15(d) and 25 Hz in 15(e). It is shown that 1/HCA follows an evolution parallel to that of the peripheral Artery Blood Pressure (ABP) shown in FIG. 15(f). HCA values calculated from data recorded at a sampling rate of 50 Hz in FIG. 15(d) and 500 Hz in FIG. 15(b) are not significantly different. This is another practical advantage that the use of HCA brings to a cardiac stimulating device such as pacemaker or defibrillator.

EXPERIMENT X

HCA's Stability Under Sensed and Paced Events

Figure 16A:
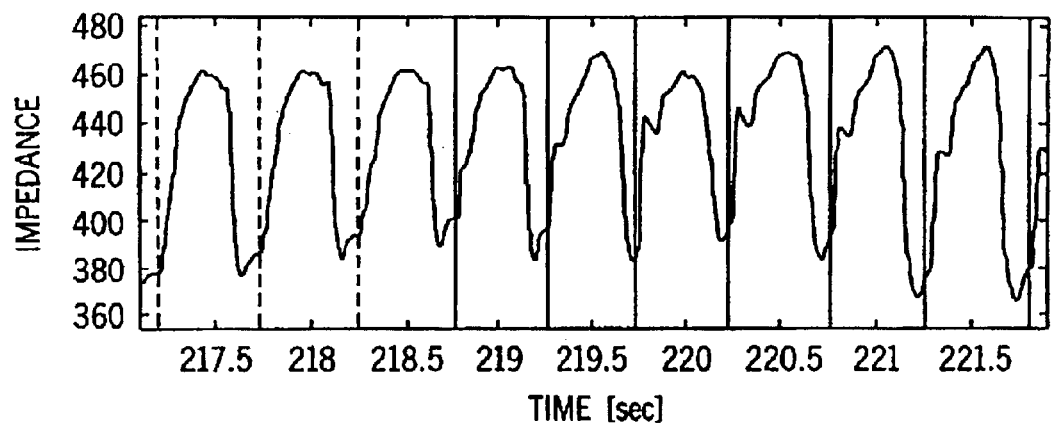
FIGS. 16(a) and 16(b) show the values of 1/HCA in (b) that correspond to the sequence of sensed and paced cardiac cycles presented in (a)
Figure 16B:
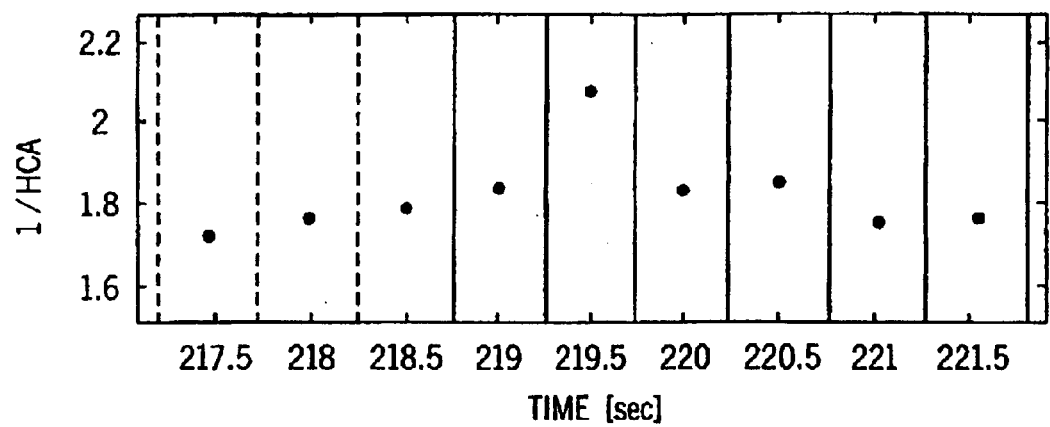

Also of importance, 1/HCA values are stable during a combination of sensed and paced events. FIG. 16(b) shows the values of 1/HCA corresponding to the sequence of sensed and paced cardiac cycles presented in FIG. 16(a). The sensed and paced events are delimited by vertical dashed and solid lines, respectively. The values of 1/HCA after sensed or paced events are not significantly different. Therefore, 1/HCA is superior to other known parameters in assessing the hemodynamic state of a patient when the pacing rate is close to the intrinsic rate, e.g. at the beginning of an exercise or during an episode of atrial fibrillation.

EXPERIMENT XI

HCA Correlates with Physiologic Reflexes During Postural Changes

Figure 17A:
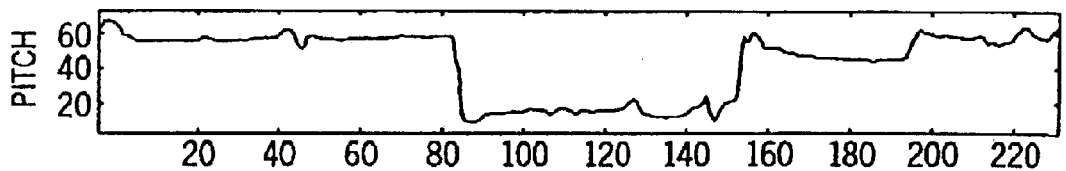
FIGS. 17(a)–17(e) are illustrations of (a) signals from a pitch sensor, (b) signals from a roll sensor, (c) maximum, mean and minimum of Telemetry Blood Pressure (TBP), (d) 1/HCA, and (e) atrial rate (bpm) recorded during postural changes.
Figure 17B:
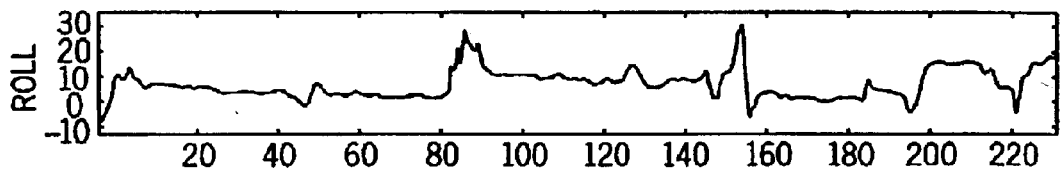
Figure 17C:
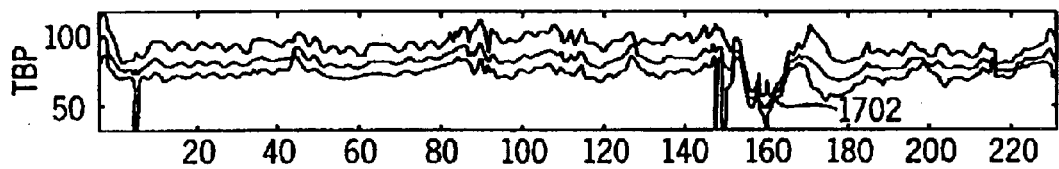

Referring to FIGS. 17(a)–17(e), an episode is recorded in an AV node ablated dog performing postural changes while being paced in VDD mode. A two-terminal configuration (RVtip to RVring) is used in this experiment. Postural changes are followed by observation of the pitch signal and the roll signal generated by sensors implanted in the dog, as shown in FIGS. 17(a) and 17(b), respectively.

Figure 17D:
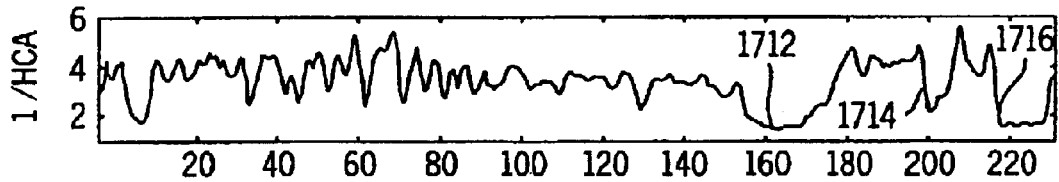
Figure 17E:
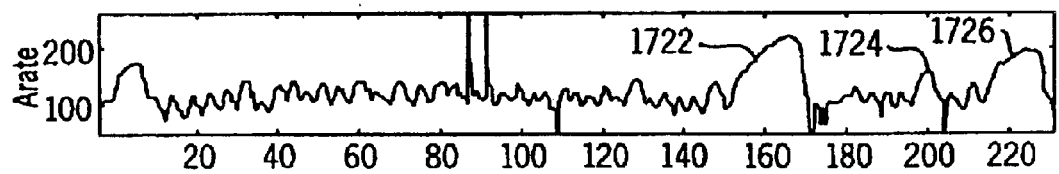

FIG. 17(d) demonstrates that the 1/HCA parameter presents a behavior coherent with that of the pressure and atrial rate. For example, an increase in atrial rate is observed in FIG. 17(e) at time point 160 (point 1722), which is associated with a decrease in telemetry blood pressure (TBP) (point 1702). This is well-known physiological reflex: the heart rate accelerates to compensate the decrease in blood pressure. The 1/HCA value presents a concomitant decrease at the same time point (point 1712). In additional to this observation, an increase in atrial rate is observed in FIG. 17(e) at time points 200 seconds (point 1724) and 220 seconds (point 1726). This increase in atrial rate is not associated with a decrease in TBP, the latter being most likely not sensitive enough to detect a transient decrease in blood pressure. However, the 1/HCA value in FIG. 17(d) presents a decrease at those time points (point 1714 and 1716), reflecting a possible transient increase in cardiac contractility. Such decrease of the 1/HCA value can, therefore, be used to advise an implantable pacemaker to increase the hemodynamically driven pacing rate, so as to follow the evolution of the intrinsic sinus activity, according to the preferred embodiment of this invention.

In summary, the main characteristics of the impedance-derived parameter HCA in accordance with the above-described embodiments of the present invention are as follows.

(1) The HCA parameter, according to the invention, correlates with physiologic demands in the body. Cardiac contractility generated either endogenously through exercise or exogenously through injection of dobutamine, leads to a corresponding decrease in 1/HCA value. The 1/HCA parameter, therefore, is used to trigger the increase in hemodynamically driven pacing rate or to limit the decrease of driven pacing rate advised by another sensor such as an accelerometer.

(2) The HCA parameter detects hemodynamic compromises resulting from inappropriate fast pacing rates; therefore, it is used to limit the upper pacing rate of an implantable bradycardia pacemaker. It works by interrupting the increase in driven pacing rate when an incremental rate increase results in a decrease in 1/HCA value, which signifies a state of hemodynamic compromise.

(3) The HCA parameter determines a Hemodynamic Upper Rate Limit (HURL) and a Hemodynamic Lower Rate Limit (HLRL), and thus, defines a Hemodynamic Pacing Range (HPR) that is compatible with the range of physiological rate. This allows a close-loop control of the pacing rate.

(4) The HCA parameter correlates with physiologic reflexes during postural changes; therefore, it provides a driven pacing rate profile compatible with the intrinsic rate profile.

(5) The HCA parameter is more resistant to noise and local pacing artifacts compared to some known impedance-derived parameters, since it is based on the impedance wave signals over the entire cardiac cycle.

(6) The effective measurement of the HCA parameter is accomplished over a broad range of sampling rates. A sampling rate as low as 50 Hz does not affect the reliability of HCA in its functions. Such robustness is advantageous for various hardware configurations.

(7) The HCA parameter remains stable throughout combinations of sensed and paced events in the heart rate. This ability renders HCA an highly appropriate parameter to assess a subject's hemodynamics when the pacing rate is close to the intrinsic rate, e.g., at the beginning of an exercise or during an episode of atrial fibrillation.

In a variant of the preferred embodiment of the present invention, a similarly impedance-derived parameter Partial Cardiac Activity (PCA) is used. PCA possesses the same characteristics as described above for HCA. The PCA parameter is a measure of the ratio of the area encompassed by a portion of an impedance waveform with a start point at a certain time of a cardiac cycle and an end point at a certain later time in the cardiac cycle and the area encompassed by the whole impedance waveform corresponding to a single cardiac cycle, which is defined by two consecutive paced and/or sensed ventricular events. The PCA parameter is further defined by the following mathematical expression [9]:

$$PCA_i = \alpha \frac{\sum_{j=N_i/\beta}^{N_i/\gamma} \left[ z_{ij} - \min_j(z_{ij}) \right]}{\sum_{j=1}^{N_i} \left[ z_{ij} - \min_j(z_{ij}) \right]} \text{ for } i = 1, \ldots, m \quad [9]$$

Where m is the number of cardiac cycles, $N_i$ is the number of samples in the i-th cardiac cycle and $z_{ij}$ is the j-th sample in the i-th cardiac cycle, and $\alpha$, $\beta$ and $\gamma$ are constants being $\beta > \gamma$.

In another variant of the preferred embodiment of the present invention, the inverse of HCA is used.

In yet another variant of the preferred embodiments of the present invention, the inverse of PCA is used.

Although the present invention has been described and illustrated in detail, it is understood that the same is by way of illustration and example only, but not to be taken by way of limitation. The scope of the present invention is defined and limited only by the terms of the appended claims.

What is claimed is:

1. A cardiac pacemaker system comprising:
   (a) an implantable lead adaptable for sensing intracardiac electrical signals and delivering high and low energy pacing therapy, wherein the lead includes two or more electrodes at various distances from each other;
   (b) a sensing module for detecting the intracardiac electrical signals;
   (c) an impedance circuit for recording intracardia impedance signals;
   (d) a microprocessor for computing an intracardiac impedance-derived parameter based on the impedance signals wherein the intracardiac impedance-derived parameter includes a ratio of a first value related to an area encompassed by a portion of an impedance waveform and a second value related to an area encompassed by a whole impedance waveform corresponding to a single cardiac cycle;
   (e) a pacing controller for adjusting a pacing therapy delivered by the system according to the impedance-derived parameter;
   (f) a pacing module for delivering pacing signals to the implantable lead according to the pacing therapy;
   (g) a sensor for generating electrical signals associated with activity related to cardiac demand; and
   (h) a second sensing module for receiving the activity related electrical signals from the sensor, wherein the pacing controller uses the intracardiac impedance-derived parameter to modify pacing therapies suggested by the sensor activity-related signals.

2. The system of claim 1, wherein the sensor for generating electrical signals associated with activity related to cardiac demand is an accelerometer.

3. The system of claim 1, wherein the intracardiac impedance-derived parameter is a Half Cycle Activity (HCA) parameter and wherein the first value related to an area encompassed by a portion of the impedance waveform is an area related to a first half of the impedance waveform.

4. The system of claim 1, wherein the intracardiac impedance-derived parameter is an inverse of the HCA parameter.

5. The system of claim 1, wherein the intracardiac impedance-derived parameter is a Partial Cycle Activity (PCA) parameter and wherein the first value related to an area encompassed by a portion of an impedance waveform is related to a portion of an impedance waveform with a start point at a certain time of a cardiac cycle and an end point at a certain later time of the cardiac cycle.

6. The system of claim 1, wherein the intracardiac impedance-derived parameter is an inverse of the PCA parameter.

7. The system of claim 1, wherein the pacing controller using the intracardiac impedance-derived parameter to modify pacing therapies suggested by the sensor includes limiting an increase in pacing rate advised by the sensor.

8. The system of claim 1, wherein the pacing controller adjusting a pacing therapy delivered by the system according to the value of the impedance-derived parameter includes determining the maximum tolerated heart rate in the event of a supraventricular tachycardia.

9. The system of claim 1, wherein the pacing controller using the intracardiac impedance-derived parameter to modify pacing therapies suggested by the sensor includes limiting a decrease in pacing rate advised by the sensor.

10. The system of claim 1, wherein the first value related to an area encompassed by a portion of an impedance waveform and the second value related to an area encompassed by a whole impedance waveform corresponding to a single cardiac cycle are determined relative to a baseline impedance value associated with respiration.

11. The system of claim 1, wherein the impedance circuit blanks the impedance signals in response to a paced event, and wherein the microprocessor pads the values of the impedance signals during blanking with a last valid impedance signal.

12. The system of claim 11, wherein the blanking occurs in response to an atrial pace marker.

13. The system of claim 11, wherein the blanking occurs in response to a ventricular pace marker.

14. The system in claim 11, wherein a duration of the blanking and padding is less than thirty milliseconds.

15. The system in claim 11, wherein a duration of the blanking and padding falls within a range of twenty to thirty milliseconds.

16. A method of monitoring hemodynamic efficacy of a patient's heart rate comprising:

computing an intracardiac impedance-derived parameter, wherein the intracardiac impedance-derived parameter includes a ratio of a first value related to an area encompassed by a portion of an impedance waveform and a second value related to an area encompassed by a whole impedance waveform corresponding to a single cardiac cycle, wherein the area encompassed by a portion of an impedance waveform and the area encompassed by the whole impedance waveform are determined relative to a baseline impedance value associated with respiration;

detecting a state of hemodynamic compromise based on the intracardiac impedance derived parameter when the rate is high; and detecting that a hemodymanic demand is not being met when the rate is low.

17. The method of claim 16, wherein the intracardiac impedance-derived parameter is Half Cycle Activity (HCA) parameter and wherein the first value related to an area encompassed by a portion of the impedance waveform is an area related to a first half of the impedance waveform.

18. The method of claim 16, wherein the intracardiac impedance-derived parameter is an inverse of the HCA parameter.

19. The method claim 16, wherein the intracardiac impedance-derive parameter is a Partial Cycle Activity (PCA) parameter and wherein the first value related to an area encompassed by a portion of an impedance waveform is related to a portion of impedance waveform with a start point at a certain time of a cardiac cycle and an end point at a certain later time of the cardiac cycle.

20. The method claim 16, wherein the intracardiac impedance-derive parameter is an inverse of the PCA parameter.

* * * * *

UNITED STATES PATENT AND TRADEMARK OFFICE
CERTIFICATE OF CORRECTION

| | | |
|---|---|---|
| PATENT NO. | : 7,062,326 B2 | Page 1 of 1 |
| APPLICATION NO. | : 10/359820 | |
| DATED | : June 13, 2006 | |
| INVENTOR(S) | : Huvelle et al. | |

It is certified that error appears in the above-identified patent and that said Letters Patent is hereby corrected as shown below:

On the Title page, item (56), under "Foreign Patent Documents", in column 2, line 1, after "3/1987" insert - - A61B 5/04 - -.

In column 14, line 1, in Claim 1, delete "intracardia" and insert - - intracardiac - -, therefor.

In column 16, line 2, in Claim 16, delete "impedance derived" and insert - - impedance-derived - -, therefor.

In column 16, line 13, in Claim 19, after "method" insert - - of - -.

In column 16, line 14, in Claim 19, delete "impedance-derive" and insert - - impedance-derived - -, therefor.

In column 16, line 17, in Claim 19, after "portion of" insert - - an - -.

In column 16, line 20, in Claim 20, after "method" insert - - of - -.

In column 16, line 21, in Claim 20, delete "impedance-derive" and insert - - impedance-derived - -, therefor.

Signed and Sealed this

Twenty-eighth Day of November, 2006

JON W. DUDAS
*Director of the United States Patent and Trademark Office*